US006369206B1

(12) United States Patent
Leone et al.

(10) Patent No.: US 6,369,206 B1
(45) Date of Patent: Apr. 9, 2002

(54) METAL ORGANOTHIOL PARTICLES

(76) Inventors: Robert D. Leone, 109 Broadway, Brooklyn, NY (US) 11211; James F. Hainfeld, 44 Bradley Dr., Shoreham, NY (US) 11786

( * ) Notice: Subject to any disclaimer, the term of this patent is extended or adjusted under 35 U.S.C. 154(b) by 0 days.

(21) Appl. No.: 09/619,343

(22) Filed: Jul. 19, 2000

Related U.S. Application Data

(63) Continuation of application No. 09/039,601, filed on Mar. 16, 1998, now Pat. No. 6,121,425, which is a continuation-in-part of application No. 08/652,007, filed on May 23, 1996, now Pat. No. 5,728,590, which is a continuation-in-part of application No. 08/282,929, filed on Jul. 29, 1994, now Pat. No. 5,521,289.

(51) Int. Cl.$^7$ ..................... C07K 16/00; G01N 33/553; A61K 39/40
(52) U.S. Cl. ................. 530/391.5; 436/525; 424/179.1
(58) Field of Search ...................... 436/525; 530/391.5; 424/179.1

(56) References Cited

U.S. PATENT DOCUMENTS

| | | | |
|---|---|---|---|
| 4,124,524 A | 11/1978 | Danielmayer et al. ... | 252/301.1 R |
| 4,313,734 A | 2/1982 | Leuvering ................. | 23/230 R |
| 5,116,759 A | 5/1992 | Klainer et al. .............. | 435/288 |

OTHER PUBLICATIONS

"A Novel Giant Palladium Cluster" by Michail N. Vargaftik, Victor P. Zagorodnikov, Igor P. Stolyarov, Iiya I. Moiseev, Vladimir A. Likholobov, Dmitry I. Kochubey, Andrew L. Chuvilin, Vladimir I. Zaikovsky, Kirill I. Zamaraev, and Galina I. Timofeeva, J. Chem. Soc., Chem. Commun., 1985.

"Nanogold™–FAB' Access Nuclear Protein", NanoNews Newsletter, Winter, 1992, Issue No. 1.

"Colloidal Gold for Multiple Staining" by J. Doerr Schott, pp. 155–157, in *Colloidal Gold, Principles, Methods and Applications*, Academic Press (1989).

FITC–Protein A–Gold Complex for Light and Electron Microscopic Immunocytochemistry, by Jürgen Roth, Moïse Bendayan, Lelio Orci, J. of Histochemistry 28: 55–57 (1980).

"Wheat Germ Agglutinin–apoHRP Gold: A New Retrograde Tracer for Light– and Electron– Microscopic Single– and Double–Label Studies", by A.I. Basbaum and D. Menetrey, The Journal of Comparative Neurology 261: 306–318 (1987).

"Probing Microtubule–Dependent Intracellular Motility with Nanometre Particle Video Ultramicroscopy (Nanovid Ultramicroscopy)", by M. DeBrabander, G. Geuens, R. Nuydens, M. Moeremans and J. DeMey, Cytobios 43 273–283 (1985).

"A 1.4 nm Gold Cluster Covalently Attached to Antibodies Improves Immunolabeling", by James F. Hainfeld and Frederic R. Furuya, The Journal of Histochemistry and Cytochemistry, vol. 40, No.2, pp. 177–184, 1992.

"Synthesis of Thiol–derivatised Gold Nanoparticles in a Two–Phase Liquid–Liquid System", by M.Brust,M. Walker, D. Bethell, D. Schiffrin, R. Whyman, J. Chem. Soc., Chem. Comm., 1994, pp. 801–802.

"Labeling Update", Product Review, Nature, vol. 356, Mar. 12, 1992, p. 177.

"Products from NANOPROBES" Catalog 1993, pp 1–12.

"Immunology: Pick of the Week", Product Review, Nature, vol. 353, Oct. 17, 1991, p. 680.

"Large Clusters and Colloids. Metals in the Embryonic State", by Günter Schmid, Chemical Reviews, 1992, pp. 1709–1726.

"Ligand–Stabilized Giant Palladium Clusters: Promising Candidates in Heterogeneous Catalysis" by Günter Schmid, J. Am. Chem. Soc. 1993, 115, 2046–2048.

"EPR on the High–Nuclearity Palladium Cluster $Pd_{561}Phen_{36}O_{200}$", J. de Aguiar, H.B. Brom, L.J. deJongh & G. Schimd, Z. Phys. D—Atoms, Molecules & Clusters 12, 457–459 (1989).

"Fresnel Effect in High Resolution Tem Imaging of Small Particles", V. Radmilovic & M.A. O'Keefe, Proc. 53rd Annual Meeting, Micros. Soc. Amer.; p. 564–565, New York. 1995.

"$Pt_{309}Phen_{36}O_{30 \pm 10}$, a Four–Shell Platinum Cluster", G. Schimd, B. Morun, J. Malm, Anew. Chem. Int. Ed. Engl. (1989) No. 6, pp. 778–780.

*Primary Examiner*—Hankyel T. Park
(74) *Attorney, Agent, or Firm*—Proskauer Rose LLP

(57) ABSTRACT

Novel metal-lipid molecules have the formula M—Or—L. M represents a cluster or colloid of atoms of Au, Ag, Pt, Pd, or combinations thereof. Or is an organic group covalently attached to the metal atoms. L represents a lipid moiety. In a preferred embodiment, M represents a cluster of about 50–70 gold atoms having a diameter of about 1.4 nm in diameter and L represents dipalmitoyl phosphatidyl ethanolamine.

25 Claims, No Drawings

METAL ORGANOTHIOL PARTICLES

This is a Continuation of Ser. No.09/039,601, filed Mar. 16, 1998, now U.S. Pat. No. 6,121,425 now allowed, which is a Continuation-In-Part of Application Ser. No. 08/652,007, filed May. 23, 1996, now U.S. Pat. No. 5,728,590, which is a Continuation-In-Part of application Ser. No. 08/282,929, filed Jul. 29, 1994, now U.S. Pat. No. 5,521,289.

FIELD OF THE INVENTION

The present invention is directed to small organometallic probes, processes for making the small organometallic probes, and applications of the small organometallic probes. In particular, the small organometallic probes of the present invention are preferably less than 0.02 micron (0.02 $\mu$m) or 20 nanometers (20 nm) in diameter, and comprise a metal cluster compound having a solid metal core, with organic groups attached to the metal core so as to impart desirable physical and chemical properties to the organometallic probes. Alternatively, the organometallic probes may comprise a metal colloid having organic groups attached to the outer surface of the metal colloid. The metal clusters or colloids may also be functionalized with other molecules attached that can be used for targeting and detecting another substance, generally, a biologically significant substance, such as an antibody, a protein, or lipid bilayer. The metal in the metal clusters or colloids is gold, platinum, silver, palladium or combinations thereof.

In one specific embodiment, the metal in the cluster is palladium or platinum and the attached organic groups are covalently attached through 1,10-phenanthroline moieties. Also disclosed is a new method for making the small organometallic probes. The method consists of a chemical procedure wherein the metal cluster compounds are prepared directly by reaction of a mixture of a salt of the cluster metal and the coordinating organic groups with a reducing agent in solution.

BACKGROUND OF THE INVENTION

Previous work by others has also described the preparation of gold and silver colloids. Such colloids do not have a fixed number of metal atoms and vary considerably in size. For example, the metal colloids can vary in size from 1 nm to 2 $\mu$m in size and may contain from about 10 metal atoms to thousands of metal atoms, depending on size. It was found that a number of proteins, such as IgG antibodies, could be adsorbed to these sol particles.

Gold colloids have been most commonly described. These conjugates have been used in electron and light microscopy as well as on immunodot blots for detection of target molecules. These conjugates have many shortcomings. Since the molecules are only adsorbed onto the colloids, they also desorb to varying extents. This leads to free antibody which competes for antigen sites and lowers targeting of gold.

Furthermore, the shelf life of the conjugates is compromised by this problem. The 'sticky' colloids also tend to aggregate. If fluorescence is used to detect the target molecules, the gold particles quench most of it. Also, the gold colloids must be stabilized against dramatic aggregation or 'flocculation' when salts are added by adsorbing bully proteins, such as bovine serum albumin. Due to the effects of aggregation and bulky additives, the penetration of immunoprobes into tissues is generally <0.5 $\mu$m. Access of the probes to internal cell structures, e.g., nuclear proteins, or to cells deeper in a tissue sample, is impeded by these properties.

Colloidal gold immunoprobes are also used in diagnosis on immunoblots. The sensitivity of these detection schemes is also reduced by problems relating to detachment of antibodies from the gold which results in a short shelf life and non-specific gold binding causing problems with background signal. The gold prepared in standard ways also has low activity due to few adsorbed antibodies and denaturation of some antibodies during adsorption.

Various metal cluster containing organic shells have also been previously described, such as $Au_{11}$ $(PPh_3)_7Cl_3$ ($PPh_3$= triphenylphosphine), and $Pd_{561}$ $L_{36}O_{200}$ (where L=1,10-phenanthroline). These metal clusters have a fixed number of metal atoms in their metal cores which range in size from ca. 0.8–2.4 nm. Most of these metal clusters are based upon reduction of metal-triphenyl phosphine or the use of 1,10-phenanthroline.

Examples of larger cluster complexes (greater than 1 nm in size) have also been reported such as clusters having the formula $M_{55}(PPh_3)_{12}X_6$ (Ph=phenyl or m-phenylsulfonyl) where M=gold, platinum and rhodium and X=halide.

For example, Barlett, P. A. et al, in "Synthesis of Water-Soluble Undecagold Cluster Compounds . . . ," *J. Am. Chem. Soc.*, 100, 5085 (1978), describe a metal cluster compound ($Au_{11}$) having a core of 11 gold atoms with a diameter of 0.8 nm. The metal core of 11 gold atoms in the undecagold metal cluster compound is surrounded by an organic shell of $PAr_3$ groups. This metal cluster compound has been used to form gold immunoprobes, for example, by conjugating $A_{11}$ to Fab' antibody fragments as well as other biological compounds.

Another metal cluster compound which has been used as a probe is Nanogold™ available from the assignee of the present application. Nanogold™ has a metal core with 50–70 gold atoms (the exact number not yet being known but believed to be 67 gold atoms) surrounded by a similar shell of organic groups ($PAr_3$) such that Ar is an aryl group into which a reactive group such as a primary amine, a maleimide, or a N-hydroxysuccinimide ester may be incorporated for conjugation to biologically significant entities including antibody IgG molecules and Fab' fragments, proteins, lipids, hormones and oligonucleotides. Nanogold™ and the smaller undecagold cluster, which contains 11 gold atoms, have been used as probes for detecting and identifying biomolecules. The metal core of Nanogold™ is 1.4 nm in diameter. The production of Nanogold is described in pending application Ser. No. 988,338, filed Dec. 9, 1992, of James F. Hainfeld and Frederic R. Furuya.

Another class of cluster complex compounds having Pt or Pd as the metal core and further having a core ranging in diameter from 1.8 to 3.6 nm is prepared by reduction of metal acetate in acetic acid by molecular hydrogen in the presence of 1,10-phenanthroline ligands. The ligated cluster is then carefully oxidized with air to neutralize the exposed metal atoms and render the compounds air-stable.

Complexes prepared by the above method and characterized by electron microscopy in order to determine the size of the metal core include a 1.81 nm core diameter platinum compound of proposed formula $[Pt_{309}phen_{36}O_{30\pm10}]$ (see Scmidt, G., Morun, B., and Malm, J.-O.; *Angew. Chem. Int. Ed. Eng.*, 1989, 28, 778), a 2.43 nm core diameter palladium compound of proposed formula $[Pd_{561}phen_{36}O_{200}]$ (de Aguiar, J. A. O.; Brom, H. B.; de Jongh, L. J., and Schmid, G.; *Z. Phys. D.:Atoms, Molecules and Clusters*, 1989, 12, 457), and a mixture of 3.16 and 3.6 nm core diameter palladium compounds with proposed formulae $[Pd_{1415}phen_{60}O_{\sim1100}]$ and $[Pd_{2057}phen_{84}O_{\sim1600}]$ respectively (Schmid, G.; Harms, M.; Malm, J.-O.; Bovin, J.-O; van Ruitenbeck, J.; Zandbergen, H. W., and Fu, W. T.; *J. Amer. Chem. Soc.*, 1993, 115, 2046), where phen is either 1,10-phenanthroline or bathophenanthroline, (1). The proposed formulae are based upon the extension of the crystal packing of metal atoms within known smaller clusters outward in discrete layers.

Although the preparation and properties vary for these metal cluster compounds having organic shells, many of these can only be synthesized in low yields, derivatization for use in coupling to biomolecules is expensive in time and effort, and again in low yields, and many of the cluster compounds are degraded rapidly by heat or various chemical reagents.

SUMMARY OF THE INVENTION

In accordance with the present invention, a new class of metal cluster compounds, and a process for making such compounds, are described. The compounds may be generally described as organothiol metal clusters, wherein the metal core is comprised of gold, platinum, silver, palladium or combinations of these metals. Prominent among the disclosed organometallic compounds is a large palladium and platinum cluster compound. The metal core of the compounds, wherein Gold is the prominent metal, is about 1.4 nm in diameter and comprises about 50 to about 70 metal atoms. There are about 12 metal atoms on the surface of each cluster, and each surface metal atom is bound to an organic group by a thiol (M—S) bond.

In another of its a the present invention is directed to mixed metal colloids and to a process for making such mixed metal colloids. While heretofore single metal colloids have been known (see description above), up to now no one has described a method for making a metal colloid with a combination of different metals the metals being selected from the group consisting of gold, silver, platinum, palladium and combinations thereof.

In another of its aspects, the present invention is directed to organic coated metal colloids, i.e., metal colloids surrounded by a shell of organic groups which are suitable for further functionaliation and covalent linking to other molecules. A process for producing such organic coated metal colloids is also described.

In another of its aspects, the present invention is directed to the organometallic clusters including the large palladium and platinum compounds described above which are covalently attached to various fluorescent molecules. This enables the preparation of dual-labeled organometallic probes which may be used to detect biomolecules using two distinct and different methods. A process for producing these organometallic probes is also described.

In another of its aspects, the present invention is directed to the organometallic clusters, including the large palladium and platinum compounds or colloids which are covalently attached to lipid molecules, and to a process for producing such compounds. The present invention is also directed to the use of such metal labeled lipids to form micelles and vesicles which are used in sensitive immunoassays, metal delivery in vivo, or other uses.

In another of its aspects, the present invention is directed to a stain based on the organometallic clusters or colloids described above, which stain may be used, for example, to stain proteins or nucleic acids after electrophoresis in gels.

In another of its aspects, the present invention is directed to the diagnostic and therapeutic medical uses of the metal conjugates described above. For example, the metals that are used can be radioactive, positron emitting, have unpaired electrons for magnetic resonance detection, or used with x-rays for absorptive or x-ray induced fluorescence detection. Other detection methods are also possible, such as mass spectroscopy. The organometallic particles may be attached to antitumor antibodies, or other targeting materials such as peptides, nucleic acids, or hormones, and used for sensitive diagnosis in vitro or in vivo. Since some isotopes produce radiations suitable for therapy or can otherwise be activated, e.g., by neutron activation, these may be used as therapeutic agents.

In another of its aspects, the present invention is directed to the development of the organometallic conjugates described above with silver developers or other toners and dyes for enhanced sensitivity or improved detection.

In yet a further aspect of the present invention, the organometallic probes described above may be used for superior ultrasensitive detection of substances, e.g., antigens or pollutants, when coupled with their use in, e.g., piezoelectric crystal mass measuring devices, detection based on changes in reflection from a surface where the particles bind, on blots (dot blots, Western or Southern blots), or by use of light, fluorescent, confocal, or electron microscopy.

The new class of organometallic cluster compounds described herein is synthesized by a novel approach and incorporates many metals such as gold, silver, platinum, and others as well as mixtures of these metals. Aside from being a novel class of clusters formed by a new process, these clusters are stable to 100° C. or higher heating, in sharp contrast to the previously known triphenyl phosphine type clusters that are of a similar size which decompose at 55° C. This heat stability creates many new areas of use for these compounds inaccessible with previous technology. Furthermore, the process is highly efficient and rapid in contrast to other synthetic routes currently known.

The field of lipids and liposomes is quite large, and covers basic biomedical research studies, diagnostics, cosmetics, drug delivery, food, catalysis and many other fields. The covalent attachment protocol described herein permits the correct attachment of the present organometallic clusters to lipids, and hence their incorporation into liposomes. They are stable, so that they may be used in a variety of further preparations of vesicles, micelles, or other constructs.

Also described herein for the first time are phospholipids and fatty acids covalently attached to gold particles. Furthermore, other lipids and lipid-like compounds can be used as well as other organometallic particles, such as the others described herein. Previously, it has not been possible to prepare gold particles conjugated to lipids. By using a covalent attachment, the products formed are indefinitely stable and can be handled in a variety of conditions for further synthesis of vesicles, micelles, or other constructs.

Also described herein is an extremely sensitive lipoimmunoassay (LIA) based on these organometallic liposomes. This improves the sensitivity and stability of currently available lipoimmunoassays.

One current form of the LIA is to encapsulate fluorescent molecules within a liposome that contains an antigen in its lipid layer. The concentration of fluorescent molecules is high enough within the vesicles such that their fluorescence is quenched. When these vesicles are exposed to serum containing the specific antibody to the antigen on the liposome and complement, the vesicles rupture and release the fluorescent molecules. When they disperse in the medium they are diluted and no longer self quench and the increase in fluorescence is measured. This test has several practical flaws. Leakage of the fluorescence over time is observed, and sensitivity could be improved. The metal-lipid conjugates disclosed in this application overcome both of these shortcomings. First, gold or another metal is formed into the unique organometallic clusters or colloids that are disclosed in this application. They are then reacted to form covalent bonds with lipid molecules. These are then treated in the usual way to form liposomes (i.e., by sonication, ether bubbling, wall peeling above the lipid phase transition temperature, etc.). This will form vesicles with, e.g., gold particles both on the inner and outer surfaces of the liposomes. The gold on the outer surface is selectively removed by treatment with potassium cyanide, β-mercaptoethanol, or other effective treatments that disintegrate the gold particles. The internal gold particles are not affected due to the lipid barrier to these reagents. After centrifugation or other purification, the vesicles (also containing antigen) are mixed with test serum as described above containing silver developer. When the vesicles lyse, the internal gold particles are exposed to the developer and a strong black color is produced. Since the gold is covalently attached, the leakage problem is circumvented and storage is greatly improved. Since silver development of gold particles has been shown to be more sensitive than fluorescence, the sensitivity is improved.

Polyacrylamide gel electrophoresis for proteins, nucleic acids and other substances is widely used in research and diagnostics. Variations are use of other gels, such as agarose, transfer of products onto immobilizing membranes, and use of probes such as nucleic acids (Southern) or antibodies (Western) to identify specific bands. In general, the bands at the end of the run are invisible and must be stained in some fashion. The two most popular protein stains are Coomassie Blue and a silver stain. Because of the weak binding to the target material over the gel, lengthy times of exposure and washing are needed, taking from 1 to 16 hours. Also, a number of steps are involved. The new stain we describe herein is vastly improved in two ways: a) development time is reduced to about 1–5 minutes, and b) the sensitivity is far greater than the other stains available. This advancement is achieved using novel organometallic compounds that more strongly interact with the target material, followed by the improved development which nucleates specifically on these organometal particles.

The use of nucleic acids (DNA and RNA) in research and medicine is very important. Many diagnostic tests are now based upon recognizing specific genetic sequences, and cloning, PCR and other molecular genetic techniques have contributed to the widespread and multifaceted applications in this area. Probes used for such tests utilize chemically attached haptens, labels or other entities which generate a signal, or are bound by other signal-producing probes. More sensitive probes are needed in order to de specific conditions earlier, using less biopsied material. The covalent attachment methods described herein are also applicable to the preparation of nucleic acid probes with the same advantages described for the antibody conjugates, and metal-containing nucleic acids may be used for other purposes such as genetic material purification.

Described herein are methods to incorporate organometallic particles into nucleic acids to provide extremely sensitive assays based upon hybridization. These metal containing nucleic acids may also be used for many other purposes, such as genetic material purification.

Labeled targeted biomolecules form the basis of diagnostic tests for many diseases and conditions. The probes of the present invention have demonstrated sensitivities significantly greater than many currently used technologies, including radioactive labeling, fluorescent labeling and colloidal gold. The increased sensitivity of the present claimed probes, most notably, those probes of the embodiment wherein the metal in the cluster is palladium or platinum, will, in turn, allow for earlier detection of harmful infections or conditions, with fewer antigen test strips needed, fewer false-positive results, and smaller biopsied specimens. Furthermore, the present invention avoids the use of radioactive or highly toxic materials, which are very costly and difficult to dispose of and impose limitations on many currently used technologies.

Unique improvements in a number of areas are now possible with the new organometallic probes described herein. For example, in medicine, molecular probes are used for diagnostic and therapeutic applications. The superior qualities of the conjugates described herein such as, covalent coupling, improved higher specific activity, various modes of detection (fluorescence, silver development, electron microscopy, X-rays, etc.) and improved sensitivity, should make these excellent candidates to replace many diagnostic detection schemes. Radioactive metals used in these clusters, colloids, and conjugates can be used for improved delivery of diagnostic or therapeutic radiation, e.g., by using antitumor antibodies. Use of positrons and other modes of detection are enhanced by the improved performance of these unique conjugates.

More specifically, current tests based on immunology are only able to detect a pathological condition after a certain concentration of antigen is present. For most conditions, such as AIDS, diagnosis at an earlier stage than current tests are capable of is important. Also, some patients have lower antibody titers and are more difficult to detect. The higher specific activity of novel conjugates described herein and their higher sensitivity in comparable tests with existing methods mean that they overcome an important shortcoming of the current technology. A further consideration in diagnosis and medicine (and most other applications) is the cost and speed of the tests performed (overall materials and labor). Since the conjugates described herein are more sensitive, fewer antigens on test strips need to be used, and fewer reagents need be used. They also develop faster than current tests due to their high sensitivity, thus taking less time to use. Since sensitivity is greater than comparable radioactive probes, more biohazards and pollutants could be eliminated by use of the conjugates described herein.

In vivo diagnostics currently also have shortcoming of sensitivity, cost, toxicity, biohazard, and environmental waste generation. As just one example, radioisotopes attached to drugs or antibodies are used, which subject the patient to radiation. The conjugates described herein can, for example, be used non-radioactively and imaged using x-ray absorption or x-ray induced fluorescence and computer tomography, giving higher resolution and lower dose to the patient.

For therapeutic applications, current technologies suffer from limitations. As just one example, radioimmunotherapy of cancer has not been thoroughly successful for a number of reasons. Enough of a suitable radioisotope must be selectively delivered to the tumor cells. Gold-189/199 is an excellent choice because of its intermediate β emission and 3 day half life. Unfortunately, it has not been stably conjugated to antibodies since it does not chelate to the usual metal chelators such as DTPA. Some progress has been made using undecagold clusters but these have been shown to have high uptake by the kidneys and show some degradation in the serum with time. One of the processes and products described in this application is a colloidal gold to which many Fab' antibody fragments can be covalently attached. This has a number of advantages for this application in radioimmunotherapy: a) this gold exhibits excellent stability properties, b) it has multiple Fab' fragments attached which improves immunoreactivity of the conjugate yielding better targeting, c) the multiple Fab's per gold particle provide a redundancy in design so that if one or more antibody fragment loses its activity either by denaturation, radiation, gold binding, or other factors, the remaining intact antibody fragments can still serve to target the radioactive gold to the tumor; d) the gold particle consists of ~100,000 gold atoms, and this number is design dependent and can be varied. The large number of isotopes carried to the tumor per antibody binding site is huge compared with other proposed radioimmunotherapies that use only one isotope per antibody. This means that orders of magnitude more dose or specific activity per antibody can be delivered. This is an important factor in achieving successful therapy. A number of significant advantages are therefore possible in this area by the conjugates disclosed herein. Other therapies, such as arthritis treatment using gold, would also be improved by the unique design, flexibility, and advantages of the novel gold structures herein disclosed.

A number of detection schemes have been devised that have improved the sensitivity or economics. One such advance is the piezoelectric detector. One mode of operation is to coat a piezoelectric crystal surface with an antigen. The crystal is part of an oscillator and its frequency of oscillation is affected by the crystal mass. When an antibody (from, e.g., test serum) binds to this surface layer, the additional molecules change the mass slightly which can be detected via a frequency change. By using, e.g., the gold conjugates described herein, e.g., the colloidal particles with covalent antibodies attached, a further solution containing gold-anti-human antibodies could be attached to the primary antibodies bound to the surface (if present in the serum) to form a "sandwich". The large mass of the gold ($\sim 5 \times 10^7$ compared with $1.5 \times 10^5$ for IgG) will greatly amplify the signal making detection levels far lower than with existing methods. A related technique uses reflection of light from a surface. When the surface is coated with a layer, even of antibody molecules, there is a change in the peak reflection angle. Use of the metallic particles (as just described) will influence to a far greater extent the change in reflection due to the strong optical properties of gold or other metal particles used. Choice of wavelength, polarization and optimizing other parameters for metal particle interaction and detection can further enhance the sensitivity.

The greater reactivity of the organometallic covalent probes can also be used to improve the detection sensitivity in other known schemes or instruments. Use in blot tests with silver enhancement of metal particles improves sensitivity over current technologies. Use of light and confocal microscopes as well as scanning and transmission electron microscopes will also benefit from these new probes which have advantages in sensitivity, small size, and high specific activity.

In accordance with one specific embodiment, a new form of large palladium and platinum compounds in which the coordinated organic groups have been modified to impart water-solubility and to enable covalent chemical conjugation to biologically important entities. The metal core ranges from about 1.8 to 3.6 nm in diameter and comprises from about 309 to out 2057 atoms. From about 36 to about 84 organic moieties, specifically 1,10-phenanthrolines, are bound to the surface metal atoms through M—N bonds, and in addition the palladium or platinum atoms are believed to be bound to between approximately 30 and 1,600 oxygen atoms. Platinum compounds larger than 1.8 nm have been observed by electron microscopy which have not been previously described. The diameter of the metal cluster, inclusive of the metal core and the organic moities ranges from about 3 to about 5 nm.

The present invention is also directed to a new method for preparing the large palladium and platinum organometallic cluster complexes described above. The new process utilizes a simpler and less hazardous procedure than currently disclosed methods. It also utilizes milder preparative conditions, which permit the introduction of a variety of modified organic groups which impart novel properties and reactivity to the clusters.

The new larger palladium and platinum organometallic compounds described above are synthesized using organic groups which confer water-solubility to the complexes and enable covalent cross-linking of the complexes to other reactive molecules, without introducing ionic charges. This feature has heretofore never been described in prior art literature. A distinct advantage of this feature is that it creates numerous opportunities for application of the above noted cluster complexes to areas which were previously inaccessible with conventional probes.

Also, the preparative process for preparing the above noted large palladium and platinum compounds results in the efficient and rapid synthesis of the contemplated compounds. While prior art processes for making conventional gold probes include dissolving reagents in acetic acid, the process of preparing the large palladium and platinum compounds of the present invention comprises dissolving the reagents in inert organic solvents, which, in turn, allows for the use of many different organic groups, which were previously incompatible with conventional methods. An added advantage realized by the large palladium and platinum compounds is that it eliminates potential hazards associated with the use of acetic acid.

A further contrast between the process noted above and prior art methods is that while previous procedures utilize hydrogen gas as the reagent to form clusters, the process of the preparing the large palladium and platinum compounds of the present invention comprises dissolving reducing agents such as sodium borohydride. This feature, simplifies significantly, the overall experimental complexity while reducing the overall expense and hazards of handling of compressed and/or flammable gas (hydrogen), which are the hallmarks of conventional processes.

The uncharged nature of the large palladium and platinum organometallic cluster probes, together with their ability to covalently link to a targeting agent also circumvents some of the same difficulties associated with colloidal gold probes of similar size.

Prior combined fluorescent and metal particle probes, e.g., where a gold particle has a fluorescent molecule attached to it, which is then conjugated to, e.g., an antibody, have been notoriously unsuccessful. This drawback can be traced to the strong quenching of fluorescence by the colloidal gold (which absorbs strongly in the visible region), together with the difficulty associated with preparing such conventional probes.

Methods for producing conventional metal particle probes have generally been fraught with the same difficulties that have visited colloidal gold probes such as their inherent tendency to "stick" or cause molecules of interest to adsorb to their respective surface, thereby preventing the molecule of interest to remain bound to the probe.

Generally, colloidal gold particles, instead of being bound covalently to the target molecule, usually adsorb electrostatically to the targeting agent. As such, these gold particles readily disassociate from the targeting agent, which, in turn, results in low labeling. Conventional colloidal gold particles are also known to 'stick' together and form large aggregates, which reduces their access to the target agent. These same gold particles have been known to adhere to components of the system they are used to investigate which, in turn, results in non-specific binding.

Described herein is a novel method of covalently linking fluorescent molecules to small organometallic particles which include the large palladium and platinum compound clusters described above. This circumvents the difficulties of the previous technology in two significant ways: first, the fluorescent molecule and the antibody or other targeting molecule (if desired) are covalently attached and do not readily "desorb." This attachment can be performed in mild physiological buffers, thus eliminating the very low ionic strength conditions necessary for colloidal gold conjugation. Thus, molecules difficult to attach to colloidal gold are simply and more stably attached by this covalent route.

Second, the chosen metal particle does not significantly quench the fluorescence, in sharp contrast to colloidal gold. In many cases, full fluorescent activity is maintained. The success of these new dual conjugates (combining fluorescence and metal, e.g., gold) permits unique applications such as fluorescent immunolabeling which is discernible by light or confocal microscopy; when cells exhibiting optimal distribution of the probe are identified, these may be processed for electron microscopy so that high resolution ultrastructure localization of antigens may be-performed. By using a dual label, there is no question as to the distributions being identical. This type of probe has long been sought by cell biologists.

Combined metal cluster and fluorescent probes have long been sought by cell biologists. As noted previously, a known disadvantage of conventional colloidal gold probes is that these probes exhibit significant fluorescence quenching and profound dissociation. This drawback can be traced to the smallness in size of conventional gold probes. As a result, it is often difficult to view these clusters in some electron microscopy applications, particularly where other electron-dense stains are used. An added advantage of the present invention, particularly the organometallic probes containing palladium or platinum is that they can be readily observed in the electron microscope even where other such stains are used. This feature is not inherent in conventional metal probes.

The highly sensitive probes of the present invention are also good candidates for use as reagents in research. The small probes make it easier to identify specific antigens in biological specimens. In addition, the small size of the organic groups of the large palladium and platinum organometallic compounds reduces the overall size of the probe, compared with prior art colloidal gold probes. This feature, in turn, allows for easy penetration of cells and tissue sections.

An added advantage of using the above noted probes in the medical and diagnostic fields is that the small size of the probes provides them with easy access to hindered sites, which is not possible with conventional probes.

For example, when comparing the probes of the present invention with Nanogold™, which is currently available from the assignee of the present application, it was noticed that Nanogold™ was able to penetrate up to 30 microns (30$\mu$) into tissue sections, while the gold colloid probes of nominally similar diameter penetrated only 0.5 microns (0.5$\mu$) of the tissue section. Enhanced penetration into cell nuclei was also observed with the probes of the large palladium and platinum clusters, while a comparably sized conventional colloidal gold probe did not access the cell nucleus at all.

DETAILED DESCRIPTION OF THE INVENTION

A brief description of the various terms appearing in the text of the present application appears hereinafter.

1. "Large Palladium and Platinum Clusters" are cluster complexes of palladium or platinum in which the central metal core is between about 1.8 nm and about 3.6 nm in diameter and contains between approximately 309 and approximately 2,057 metal atoms. The surface atoms are bound to a variety of substituted 1,10-phenanthroline ligands, numbering from about 36 to about 84 in total, and also to oxygen atoms, believed to number between about 30 and about 1,600, which stabilize the surface and block further surface reactions. The diameter of the metal cluster inclusive of the internal metal core and the organic moities varies from about 2 to about 5 nm.

2. The 1,10-phenanthroline ligands used to prepare the large palladium and platinum clusters, listed above in #1, are modified by the introduction or specific chemical functional groups at either the 4 and 7-positions, or the 5-position. These substituents are capped either with reactive groups, including primary amines, maleimides, and sulfo-NHS esters, which can be covalently bound to other molecules, or with solubilizing groups including 1,2-diols or p-phenylsulfonates, or with biologically compatible but inert functionaries including N-methylcarboxamides or acetamides.

3. Reactive groups incorporated into coordinated ligands may be used to attach the cluster covalently to antibodies, proteins, lipids, peptides, drugs, DNA, RNA, or any other biologically active molecule with a group which may be cross-linked. This circumvents the requirements for low salt concentrations which prevent conjugation of many molecules-such as IgMs-with colloidal gold.

4. Combined (bifunctional) fluorescent and metal particle probes comprising the large palladium and platinum cluster listed above (according to #1) can be synthesized having the formula $M_n(OrF)_m(Or'T)_l(Or'')_pO_q$, where M is the metal core consisting of platinum or palladium of which the surface atoms may be covalently bonded to a shell of organic groups (Or, Or', Or"). Or and Or' are covalent coupling moieties, specifically 1,10-phenanthrolines containing cross-linkable groups such as amines, carboxyls, maleimides or N-hydroxysuccinimide esters, F is a fluorescent molecule (fluorescein, Texas Red, rhodamine, aminomethyl coumarin, etc.), and T is an optional targeting molecule such as an antibody, peptide, drug, etc. Or, Or' and Or" may be the same or different. The subscripts l, m, n. p and q indicate that multiple copies of each moiety are possible and include mixtures of different fluorescent groups, organic groups and targeting molecules for multifunctional conjugates. A specific example is the following:

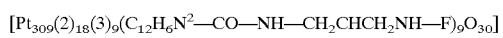

wherein $C_{12}H_6N_2$—CO—NH—CH$_2$CH$_2$CH$_2$NH—F refers to a ligand exemplified by formula 3, after reaction of the primary amine with an activated carboxylic ester of fluorescein.

5. A new method for the chemical preparation of cluster complexes according to #1 comprises dissolving a divalent salt of palladium or platinum MXX', wherein M is palladium or platinum and X and X' are acetate, chloride, bromide, iodide and acetyl-acetonate anions, and a mixture of Or, Or'and Or" in the mole ratio desired in the final cluster, in either N, N'-dimethylacetamide or in a mixture of ethanol, benzene, dichloromethane and water. Thereafter, the resulting product is reacted with a solution of a reducing agent such as sodium borohydride or a hydride-transfer reagent of general formula M'EHRR'R" where M' represents sodium or lithium, E represents boron or aluminum, H represents hydrogen, and R, R' and R" are the same or different and are hydrogen or straight-chain or branched,cain hydrocarbons with 1–10 carbon atoms, dissolved in N, N'-dimethylacetamide or in another inert solvent.

The above process, essentially, eliminates the hazards and experimental complexity associated with using hydrogen gas or acetic acid, both of which are required by the conventional technology. Also, the reaction conditions are compatible with a variety of Or, Or' and Or" groups or their-precursors.

6. After cluster formation, cross-linking to other molecules T may be achieved by a variety of methods. If Or' is a primary amine-containing moiety, this is converted to a maleimide or N-hydroxysuccinimide ester and reacted with a molecule which contains either a thiol or a primary amine; alternatively, it may be reacted directly, for example with an activated ester or with an aldehyde group in the target molecule. This results in the formation of a targeted probe which may either be visualized directly in the electron microscope, or rendered visible in the light microscope or other optical systems by a process of silver enhancement.

7. "Thiol gold clusters" are novel gold dusters produced by a novel synthesis. The procedure is: form an organic-gold complex by reacting a compound containing a thiol with gold in solution. A second equivalent is also added of the thiol compound. Finally the gold organic is reduced with $NaBH_4$ or other reducing agents and organometallic particles are formed. These have the general formula AunRmR'l . . . , where n, m, and l are integers, R and R' are organic thiols, (e.g., alkyl thiols, aryl thiols, proteins containing thiol, peptides or nucleic acids with thiol, glutathione, cysteine, thioglucose, thiolbenzoic acid, etc.) and the ellipsis indicates that one or more organic thiols may be used. With two equivalents of organic thiol compound, clusters with gold cores ~1.4 nm are formed with many organic moieties. The organic moiety may then be reacted by usual reactions to covalently link this particle to antibodies, lipids, carbohydrates, nucleic acids, or other molecules to form probes. Mixtures of organic thiols may be used to provide mixed functionality to the clusters. These organo-gold clusters are stable to heating at 100° C.

8. Combined (bifunctional) fluorescent and metal particle probes wherein the metal in the metal clusters is gold, platinum, palladium, silver or combinations thereof (according to #7, described above) have been synthesized and have the following formula:

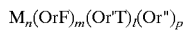

wherein M is a metal core consisting of multiple metal atoms (Au, Pt, Ag, Pd) that can be mixed, covalently bonded to a shell of organic groups (Or, Or', and Or"). Or and Or' are organic coupling moieties, (e.g., triphenyl phosphine 1,10 phenanthrolines, triphenyl phosphine or phenanthrolines containing linkable groups such as amines or carboxyls, triphenyl phosphine or 1,10, phenanthrolines containing reactive groups such as maleimides or N-hydroxysuccinimide esters, $P(C_6H_4—CO—NH—(CH_2)_3—NH_2)_3$, $P(C_6H_4—CO—NH—CH_3)_2(CH_6H_4—CO—NH—(CH_2)_3—NH_2)$, $P(C_6H_4—CO—NH—(CH_2)_3—NC_4O_2H_2)_3$, $P(C_6H_4—CO—NH—(CH_2)_3—NH—(CH_2)_6—CO_2—NC_4O_2H_4)_3$, etc.), Or" is an organic group (e.g., triphenyl phosphine, 1,10 phenanthrolines, $P(C_6H_4—CHOH—CH_2OH)_3$, $P(C_6H_4—CO—NH—CH_3)_3$, $P(C_6H_5)_3$, $P(C_6H_4SO_3)_3$, etc.), part of the metal cluster, F is a fluorescent molecule, (e.g., fluorescein, rhodamine, aminomethyl coumarin, Texas Red, etc.) and T is an optional targeting molecule such as antibody, peptide, drug, etc. Or, Or', and Or" may be the same or different. The subscripts l, n, m and p indicate that multiple copies of each moiety are possible and include mixtures of different metals, fluorescent groups, organic groups and targeting molecules for multifunctional conjugates. A specific example of this is:

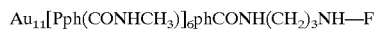

wherein ph is a phenyl group, and F is a fluorescent molecule.

A process to produce the above noted multifunctional metal particle according to #5, supra, comprises synthesizing a metal cluster or metal colloid having one or more reactive groups such as an amine or carboxyl. The particles are thereafter reacted to covalently link a fluorescent molecule such as fluorescein, Texas Red, rhodamine, or aminomethyl coumarin, and optionally a targeting or other molecule is covalently attached such as an antibody or antibody fragment, a peptide, streptavidin, or other proteins, a nucleic acid (RNA or DNA), drugs, hormones, or other molecules. Alternatively, the fluorescent groups may be incorporated into ligands which are then used to prepare the cluster.

9. The thiol-gold preparation described in #8 above may be altered such that a larger molar ratio of organic thiol to gold is used. Ratios approximately 2:1 or below 1:2 result in organic-gold colloids whose size depends on this ratio. These are useful when large gold particles are desired.

10. The organic thiol-gold preparations described in #'s 8 and 9 above may be made using a similar process with alternatives metals to gold, e.g., platinum, silver, palladium and other metals.

11. The organic thiol-metal particles described in #'s 8, 9 and 10 above may be made using mixtures of metal ions, e.g., gold and silver, resulting in mixed metal clusters.

12. A novel process has been developed for coating colloidal particles (of various types including gold, silver, palladium, platinum and other metals) with organic moieties having groups suitable for covalently attaching additional molecules, such as antibodies, nucleic acids, lipids, peptides, and other proteins. The process consists of synthesizing the metal colloid in the presence of a suitable polymer, e.g., $HAuCl_4$ (0.01%) in 0.05 M sodium hydrogen maleate buffer (pH 6.0), with 0.004% tannic acid. The polymer may be chosen from a linear or branched group with functional groups attached, such as polyamino acids, polyethylene derivatives, other polymers, or mixtures thereof. Optimal molecular weight of the polymer varies with the specific ones chosen. A second method is to synthesize the metal particle first, e.g., by combining 0.01% $HAuCl_4$ with 1% sodium citrate with heating. Once gold colloid is formed of the desired size, it is coated with one of the above polymers by mixing the two together and optionally warming to 60–100° C. for several minutes. The polymer coating may be further stabilized by a) microwave heating, b) further chemical crosslinking, e.g., by glutaraldehyde or other linkers, or by continued polymerization adding substrate molecules for a brief period. Use of N, N'-methylene bis acrylamide, for example, can covalently further stabilize the polymer coating. Photocrosslinking may also be used.

The functionalized polymer coating may now be used to covalently attach proteins, peptides, antibodies, lipids, carbohydrates, nucleic acids, drugs, hormones, or other substances. This has the advantage that this step may be done mildly, in physiological buffers if desired, using standard crosslinking technology. This eliminates the usual restriction that conjugation must be performed in very low ionic strength buffers, which precludes attachment of certain molecules such as many IgM's which cannot withstand the low ionic strength requirement.

13. Lipid molecules (fatty acids, phospholipids, or others) are covalently attached to metal particles (clusters or coated reactive colloids). This process uses a reactive lipid derivative, e.g., a sulfonyl chloride or anhydride, which is reacted with an amino group, for example, on the metal particle. Alternatively, organic groups on the metal particle or lipid may be reacted with bifunctional crosslinkers which are then reacted with the other species. Another process is to pre-synthesize the organic components of the metal particles (e.g., phosphine or polymers) with lipid molecules attached and then to use these organo-lipids in constructing the functionalized metal particle.

The general formula for the product is:

M—Or—L wherein M is the metal particle (either cluster or colloid of Au, Pt, Ag, Pd, and combinations), Or is an organic group of the organometallic particle (such as, phosphine containing linkable groups, polymers containing linkable groups, $P(C_6H_4\text{—CO—NH—}(CH_2)_3\text{—NH}_2)_3$, polyethyleneimine, polyacrylamide hydrazide, polylysine, etc.), and L is the lipid moiety.

14. A novel gel stain product is a metal (preferably gold) cluster of the form described in #8 above using appropriate organic thiols. The thiols are preferably o-thiol benzoic acid, glutathione, and thioglucose, although others may be used. The general formula describing the product is:

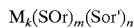

$M_k(SOr)_m(Sor')_n$ where M is the metal, S is sulfur, Or and Or' are organic groups (such as proteins or nucleic acids containing thiols, most other organic thiols, glucose, benzoic acid, glutathione, cholesterol, etc.), and k, m and n are integers. The ellipsis indicates that one or more different (Sor) groups (organic thiols) may be attached per metal core.

The process for a protein polyacrylamide gel is as follows: mix the organometallic particle with the protein sample with or without SDS (sodium dodecyl sulfate), for native or denaturing gels; if a reducing gel is desired, the protein is first reduced with a reductant, preferably β-mercaptoethanol, followed by a thiol blocking agent, preferably iodoacetamide, before adding the metal stain. The sample is heated briefly (e.g., one minute), loaded onto the gel and run normally. Stain development is effected by soaking the gel in a silver enhancement medium (e.g., $AgNO_3$ with hydroquinone) for several minutes followed by water or fixing washes.

15. The organometallic particles described above may be covalently incorporated into nucleic acids by several techniques. One is via synthesis of a metal particle attached to a nucleic acid base or analogue that has its other functional groups protected so that it is compatible with automated nucleic acids synthesis, such as use of phosphoramadite chemistry. A second approach is to incorporate appropriate organometallic base analogs into nucleic acids enzymatically. A third method is to react activated organometallic clusters or colloids with functional groups incorporated into nucleic acids (such as primary amines). A fourth approach is to use organometallic particles that contain photoactive group(s) that then covalently attach to the nucleic acids when light activated.

The present invention shall be described in greater detail with reference to the examples appearing hereinafter.

EXAMPLES

Preparation of Fluorescent and Gold Immunoprobes
1. Preparation of Fluorescein-Conjugated Nanogold Using Fluorescein-Phosphine A tris (aryl) phosphine ligand bearing a single fluorescein substitutent, and a second tris (aryl) phosphine ligand bearing a single primary amine, were mixed with tris (p-N-methylcarboxamidophenyl) phosphine in the ratio 2:1:5. Ninety mg of this ligand mixture in 25 Ml of methanol (an estimated twelve-fold molar excess) was added to a solution of freshly prepared Nanogold (product from 0.4 g of gold (I) triphenylphosphine chloride) in dichloromethane (25 Ml) and stirred at room temperature overnight.

The reaction mixture was extracted with 0.02 M ammonium acetate with acetic acid, Ph 5.8, in 20% isopropanol/water (3×150 Ml), then evaporated to dryness, redissolved in DMSO (2 Ml) and 0.6M triethylammonium bicarbonate in 20% isopropanol/water. The fluorescein-substituted-Nanogold was isolated by gel filtration, using a coarse gel in a large column (length=120 cm, internal diameter=2.5 cm, volume=590 Ml), eluting with 0.6M triethylammonium bicarbonate in 20% isopropanol/water. The brownish-green product is the first species to be eluted. Yield was 820 nmol. UV/visible data suggested that the product incorporated 6 fluorescein groups per cluster.

2. Preparation of Fluorescein-Conjugated Undecagold Using Fluorescein-Phosphine

Gold (I) cyanide (31 mg, 0.14 mmol) was stirred with a 4:1:1 mixture of a tris (aryl) phosphine ligand bearing a single fluorescein substitutent, a second tris (aryl) phosphine ligand bearing a single primary amine, and tris (p-N-methylcarboxamidophenyl) phosphine (105 mg, 0.14 mmol) in a mixture of methanol (3 Ml) and ethanol (5 Ml) for 4 hours. Sodium borohydride (3 mg, 0.1 mmol) in ethanol (2.0 Ml) was added dropwise over 30 minutes, then 8 drops of acetone were added to stop the reduction. The orange-brown solution was added to 10 Ml of aqueous 3.0M sodium chloride, stirred for 30 minutes, then evaporated to dryness, stirred with methanol (20 Ml) and filtered through a medium porosity glass frit in order to exchange the coordinated cyanide ligands for chlorides.

The cluster was separated from uncoordinated ligands and other smaller molecules by chromatography over a coarse gel filtration column (dimensions as described in the fluorescent Nanogold preparation) eluting with 0.6 M triethylammonium bicarbonate buffer in 5% methanol/water. The pale greenish-orange cluster (yield close to 50 nmol) is eluted first, followed by uncoordinated ligands and smaller molecules. Calculations based on the UV/visible absorption spectrum suggested incorporation of 5.5 fluorescein groups per undecagold.

3. Preparation of Texas Red-conjugated Nanogold

Nanogold was prepared as described for fluorescein-conjugated analog, except that a different mixture of phosphine was used to perform the ligand exchange on the freshly made compound. A 2:1:8 mixture of a phosphine bearing a single primary amine, a phosphine containing a single primary amine protected with a t-Boc group, and tris (N-methylcarboxamidophenyl) phosphine. The protected cluster was isolated in the same manner as the fluorescein-conjugated analog.

400 nmol of protected Nanogold was evaporated to dryness five times from methanol to remove triethylammonium bicarbonate, then dissolved in isopropanol (0.2 Ml) and 0.1 M sodium borate buffer, Ph 9.0 (0.4 Ml). This solution was added to a solution of Texas Red sulfonyl chloride (8-fold excess, 2.1 mg) in isopropanol (0.2 Ml) and the mixture incubated at 4° C. for 1 hour. The products were separated by coarse gel filtration (GH25 gel, Amicon, using column with length=50 cm, internal diameter=0.66 cm, volume=16 Ml) eluting with 0.6 M triethylammonium bicarbonate in 50% isopropanol/water. The dark blue product eluted in the void volume: it was evaporated to dryness from methanol five times, then the t-Boc protecting group was removed with 0.1 M hydrochloric acid in methanol (1 hour). The solution was neutralized with triethylammonium buffer, evaporated to dryness and re-chromatographed (GH25 gel, buffer as above) to remove triethylammonium chloride. Final yield was 170 nmol (43%). Labeling calculated from the UV/visible spectrum was 1.17 Texas Red groups per cluster.

4. Conjugation of Fluorescein-Nanogold or Undecagold to Antibody Fab' Fragments F(ab')$_2$ antibody fragments (1.0 mg) were reduced with 40 Mm mercaptoethylamine hydrochloride in 0.1 M sodium phosphate at Ph 6.0, with 5 Mm EDTA (1.4 Ml) for 1 hour at room temperature. Then the Fab' fragments were separated on a coarse gel filtration column (GH25, Amicon: length=50 cm, internal diameter=1.0 cm, volume=40 Ml), and eluted with 0.02 M sodium phosphate, Ph 6.5, with 150 Mm NaCl and 1 Mm EDTA.

Fluorescein-conjugated Nanogold (250 nmol) was evaporated to dryness five times from methanol solution to remove any triethylammonium bicarbonate, then dissolved in DMSO (0.5 Ml) and 0.1 M sodium phosphate buffer, Ph 7.5 (0.9 Ml) and added to a solution of a 100-fold excess of N-methoxycarbonylmaleimide (NMCM, 8 mg) in DMSO (0.1 Ml), mixed and incubated at 0° C. for 30 minutes. Maleimido-[Nanogold-fluorescein] was separated from unreacted NMCM on a coarse gel filtration column (GH25, Amicon: length=50 cm, internal diameter=1.0 cm, volume= 40 Ml), eluted with 0.02 M sodium phosphate, Ph 6.5, with 150 Mm NaCl and 1 Mm EDTA in 10% isopropanol/water. Maleimido-[Nanogold-fluorescein] was eluted in the excluded volume; a 5-fold excess was added to the Fab' fragments and the mixture mixed and incubated at 4° C. overnight. The product was concentrated to 0.5 Ml using centrifuge membrane concentrators with a 30,000 molecular weight cutoff (Centricon-30, Amicon), then isolated by gel filtration chromatography using a medium gel (Amicon GCL-90: Column length=50 cm, internal diameter=0.66 cm, volume=16 Ml). 0.02 M sodium phosphate with 150 Mm sodium chloride, Ph 7.40, was used as the eluent. The labeled Fab' fragments eluted first, followed by unbound fluorescein-Nanogold. The process was repeated once for highest purity of product.

[Au$_{11}$-Fluorescein] labeling was conducted in the same manner, except that the buffer used to separate the activated fluorescein-gold was prepared as a solution in 40% DMSO/water.

5. Labeling of Streptavidin with Fluorescein-Conjugated Nanogold

Fluorescein-conjugated Nanogold (250 nmol) was evaporated to dryness five times from methanol to remove any triethylammonium bicarbonate, then dissolved in DMSO (0.4 Ml) and 0.02 M HEPES-NaOH buffer, Ph 7.5 (0.9 Ml) and added to a solution of bis (sulfo-N-hydroxysuccinimidyl) suberate (BS$^3$)(250-fold excess: 38 mg in DMSO (0.1 Ml). The solution was mixed thoroughly, incubated at room temperature for 1 hour and 25 minutes, then sulfo-NHS-[Fluorescein-Nanogold] was separated from excess (BS$^3$) by chromatography on a coarse gel filtration column (GH25, Amicon: length=50 cm, internal diameter=1.0 cm, volume=40 Ml), eluting with 0.02 M HEPES-NaOH, Ph 7.5, in 20% isopropanol/water. Activated fluorescein-Nanogold was the first species to be eluted, and was mixed in 12-fold excess to a solution of streptavidin in an aqueous solution of the same buffer. The mixture was incubated at 4° C. overnight, then reduced to 0.5 Ml by membrane centrifugation (Centricon-30, Amicon) and purified twice by gel filtration (Amicon GCL-90 gel: Column length=50 cm, internal diameter=0.66 cm, volume=16 Ml) eluted with 0.02 M sodium phosphate buffer, Ph 7.4 with 150 Mm NaCl. Labeled streptavidin is the first species to be eluted.

6. Labeling of Antibody Fab' Fragments with Texas Red-Conjugated Nanogold

Antibody reduction and fluorescent gold label conjugation were conducted as described for fluorescein-Nanogold. Texas Red-Nanogold (200 nmol) was converted to the maleimide form by reaction with a 100-fold excess of NMCM (3 mg) for 30 minutes at 0° C. in DMSO (0.30 Ml), and 0.1 M sodium phosphate buffer at Ph 7.5 (0.45 Ml); the activated label was isolated by chromatography over a coarse gel filtration column (GH25, Amicon: length=50 cm, internal diameter=0.66 cm, volume=16 Ml), eluted with 0.02 M sodium phosphate with 150 Mm sodium chloride and 1 MM EDTA in 50% isopropanol/water; gold-containing fractions were added in fivefold excess to Fab' fragments, prepared from F(ab') fragments as described in Example 3, and incubated at 2–8° C. overnight. The product was isolated on a medium gel filtration column (Amicon GCL-90: 50 cm, internal diameter=0.66 cm, volume=16 Ml), eluting with 0.02 P 7.4+150 mm NaCl. The blue-grey product was the first species to be eluted.

7. Conjugation of Hoescht-33258 to Nanogold

Cross-linking was performed with 1,1'-carbonyldiimidazole (CDI). Hoescht-33258 (3 mg) was dissolved in 0.5 Ml DMSO with a stoichiometric amount of CDI and incubated at room temperature for 30 minutes, then polyamino-1.4 nm gold cluster (150 nmol, giving 100fold excess of dye) in DMSO (0.4 Ml) was added and incubation continued for a further 1 hour at room temperature. The reaction mixture was then diluted with deionized water to 20% DMSO and concentrated three times to minimal volume using membrane centrifugation (10,000 MW cutoff). The solution was switched to a 30,000 MW cutoff membrane concentrator and centrifuged to minimal volume a further 8 times; no 1.4 nm gold was observed to pass through the membrane. The concentration of fluorescent dye in the filtrate was determined spectrophotometrically, and by the end of the eighth centrifugation had fallen to less than half the concentration of 1.4 nm gold particles remaining in the retained solution, diluted to the same volume. The ratio of dye molecules to gold clusters, in the final product was estimated spectrophotometrically to be 1.2.

Preparation of Gold-Labeled Dipalmitoyl Phosphatidyl Ethanolamine (DPPE)

8. Labeling of DPPE with Freshly Activated 1.4 nm Gold

Activation of the gold particles was conducted in methanol with a small amount of triethylamine added, until the reading of a Ph meter inserted into the solution was between 7.5 and 8.0, to promote the reaction. 300 nmol of monoamino 1.4 nm gold, isolated by ion exchange chromatography (in 0.6 M triethylammonium bicarbonate buffer in 20% isopropanol/water) was evaporated to dryness five times from methanol to remove the volatile buffer, then dissolved in 1.5 Ml of triethylamine-treated methanol in which a 500-fold excess of bis(sulfo-succinimidyl) suberate (86 mg) was dissolved. This mixture was incubated at room temperature for 1 hour 30 minutes. The activated 1.4 nm gold was separated over a coarse gel filtration column (Amicon, GH25: length=50 cm, internal diameter=1.0 cm, volume=40 Ml), eluted with methanol; the dark brown activated Nanogold is the first species to elute. Fractions containing uncontaminated activated Nanogold were combined to yield 180 nmol of activated gold, in 4 or 6 Ml. A solution of DPPE (100-fold excess: 12 mg) in one-half this volume of trichloromethane was added and the mixture incubated at 4° C. overnight.

The reaction mixture was evaporated to dryness, and stirred with 0.02 M ammonium acetate, Ph 5.80 (50 Ml) to extract any unreacted Nanogold; this suspension was extracted three times with chloroform (15 Ml). The combined chloroform extracts were evaporated to dryness, dissolved in a 2:1 methanol/chloroform mixture, and separated on a column identical to that used above for the Nanogold activation, eluted with the same solvent mixture. The dark brown Nanogold-DPPE conjugate is the first species to be eluted; unconjugated DPPE is eluted later.

9. Labeling of DPPE with Lyophilized Mono-sulfo-NHS-1.4 nm Gold (Nanogold)

60 nmol of lyophilized monofunctional sulfo-NHS-Nanogold (Nanoprobes, catalog number 2025: two vials) was redissolved in methanol (2 Ml) with a drop of triethylamine, and added to a 150-fold excess of DPPE in a 2:1 methanol/chloroform mixture with a small amount of dichloromethane (4 Ml), mixed thoroughly and incubated overnight at 4° C.

The reaction mixture was evaporated to dryness, then redissolved in a 2:1 methanol/chloroform mixture (0.8 Ml), filtered, and chromatographed over a coarse gel filtration column (Amicon GH25: length=50 cm, internal diameter=0.66 cm, volume=16 Ml), eluting with 2:1 methanol trichloromethane. The brown DPPE conjugate is the first species to be eluted; colorless unreacted DPPE is eluted later.

10. Preparation of Undecagold-DPPE

Both the activation reaction of the gold, and chromatographic separation of activated gold, are conducted in a basic methanolic buffer, prepared as follows: sufficient HEPES to give 200 Ml of a 0.02 M solution (0.956 g) are suspended in methanol (200 Ml), and triethylamine added slowly, dropwise, until all the HEPES is dissolved. A Ph electrode was then inserted into the solution, and dilute triethylamine in methanol was added until the reading on the Ph meter was between 7.6 and 8.0.

Ion exchange-isolated monoamino undecagold (150 nmol, by UV/visible absorption spectroscopy, dissolved in aqueous 0.6 M triethylammonium bicarbonate buffer in 5% methanol) was evaporated to dryness five times from ethanol to remove the volatile buffer. It was then dissolved in 0.6 Ml of the methanolic HEPES buffer and added to a solution containing a 200-fold excess of bis(sulfo-succinimidyl) suberate (17 mg) in methanolic HEPES buffer (0.2 Ml) to give a total volume of 0.8 Ml. The solution was mixed thoroughly, then incubated at room temperature in a small polyethylene vial for 1 hour and 30 minutes. Activated undecagold was separated from excess BS$^3$ using a coarse gel filtration column (Amicon GH25; length=50 cm, internal diameter=0.66 cm; volume=16 Ml), eluting with methanolic HEPES buffer prepared earlier. The activated undecagold cluster is the first species to be eluted. Fractions containing uncontaminated activated undecagold were pooled, to yield about 80 nmol of activated undecagold in 2 or 3 Ml. This was then added to a solution of a 100-fold excess of DPPE (5.4 mg) in a volume of chloroform equal to one-half the volume of the activated undecagold (1 or 1.5 Ml), mixed thoroughly, and incubated overnight at 4° C.

The mixture was then evaporated to dryness, and shaken with a water/chloroform mixture to remove unreacted undecagold; the aqueous layer was removed and the process repeated twice. The organic layer and solid material accumulated at the phase boundary were then evaporated to dryness, dissolved in a 1:1 methanol/dichloromethane mixture (0.8 Ml), and separated on a column identical to that used above to separate activated undecagold. The eluent was a 1:1 methanol/dichloromethane mixture. The Undecagold-DPPE conjugate is the first species to be eluted, and is orange in color; colorless unconjugated DPPE is eluted later.

Golden Lipids

Preparation of Alkylamido-1.4 nm Gold Cluster Derivatives

General: Monoamino-1.4 nm gold cluster is reacted in excess with alkyl acid chloride or alkyl acid anhydride in dichloromethane. The unreacted gold cluster was extracted from the reaction mixture into aqueous buffer and the product was purified from alkyl carboxylic acids, produced from the hydrolysis of unreacted acid derivatives, by size exclusion chromatography. The alkyl carboxylic acid derivatives include nonanoyl chloride, decanoyl chloride, decanoic anhydride, lauroyl chloride, lauric anhydride, palmitoyl chloride, palmitic anhydride, heptadecanoyl chloride, stearoyl chloride, and stearic anhydride.

11. 300 nmol of monoamino 1.4 nm gold cluster, isolated by ion exchange chromatography and removal of volatile buffer salts by evaporation, was placed in 3 ml dichloromethane and treated with 200 nmol palmitoyl chloride. The mixture was stirred for 1 hour and then washed three times with 0.1 M sodium phosphate buffer Ph 6.5. The remaining reaction mixture was evaporated to dryness, redissolved in a 2:1 methanol/chloroform, and separated on a gel filtration column (Amicon GH25) eluting with 2:1 methanol/chloroform. The first to elute is the dark brown palmitamido gold cluster.

Preparation of Large Platinum and Palladium Cluster Immunoprobes

12. Preparation of Functionalized 1–2 nm Platinum Cluster Ligands

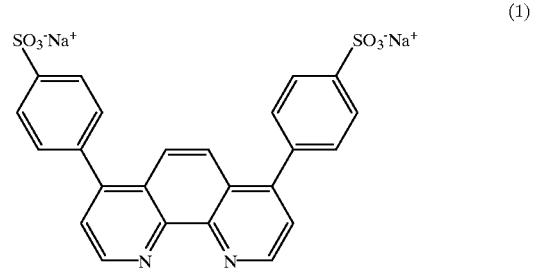

(1)

-continued

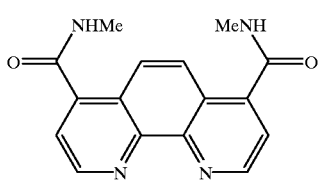
(2)

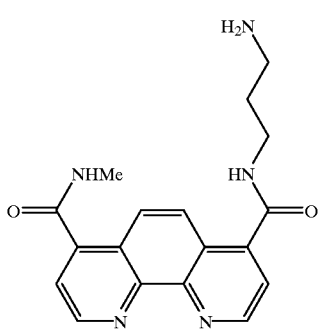
(3)

Note: ratio of N-methylcarboxamide:3-aminopropylcarboxamide in ligand (3) is between 5:1 and 10:1.

From platinum (II) acetylacetonate and bathophenanthroline: A mixture of $Pt^{II}(acac)_2$ (0.20 g, 0.5 mmol), bathophenanthroline (1:35 mg, 0.064 mmol) and 5–10:1 mixed ligand (3:5 mg, 0.016 mmol) was stirred in glacial acetic acid (20 Ml) under a slow flow of nitrogen. Meanwhile sodium borohydride (2.3 g) was dissolved in 2-methoxyethyl ether (diglyme: 30 Ml) and a 1:1 mixture of ethanol/water (20 Ml) was added dropwise over 30 minutes; the hydrogen generated from this solution was bubbled into the reaction mixture. After 30 minutes no color change was observed: therefore, a small amount of platinum (II) chloride (~0.05 g) suspended in acetic acid (1 Ml) was added and stirring continued. $H_2$ bubbling was continued for a further 4 hours, during which time the solution darkened from yellow to green and a greenish-black precipitate was formed. The solution was then aerated for 2 hours by blowing air into the flask.

The contents of the reaction vessel were evaporated to dryness, and the greenish-black solid extracted with DMSO (0.5 Ml) and 0.6 M triethylammonium bicarbonate in 20% isopropanol/water (1.5 Ml), filtered, then separated over a coarse gel filtration column (GH25, Amicon) eluting with 0.6 M triethylammonium bicarbonate in 20% isopropanol/water. A dark greenish-brown compound was eluted in the void volume, and pale yellow species later. Electron microscopy of the greenish-brown compound showed metal particles 1–2 nm in diameter.

From Platinum (II) chloride and substituted phenanthrolines: A mixture of platinum (II) chloride (0.5 mmol, 126 mg), ligands 2 (14.8 mg) and 3 (5.1 mg) were stirred in glacial acetic acid (25 Ml) for 6 hours and heated to 100° C. to partially dissolve the solids. After cooling to room temperature overnight, hydrogen (generated as described above) was bubbled slowly through the reaction mixture for 3 hours; the color darkened from brown to greenish-black. The reaction mixture was then poured into a glass beaker and stirred overnight while air was bubbled through the solution. All the acetic acid was removed to leave a greenish-black solid. This was then extracted into DMSO (0.5 Ml) and 0.6 M triethylammonium bicarbonate in 20% DMSO/water (1.5 Ml), filtered, and separated on a coarse gel filtration column (GH25, Amicon) eluting with 0.6 M triethylammonium bicarbonate in 20% DMSO/water. A brownish-green species was eluted in the void volume.

13. Preparation of functionalized 1.8–3.6 nm platinum clusters

Representative examples of the ligands of type Or' include at least one of maleimide, N-hydroxysuccinimide, and sulfo-N-hydroxysuccinimide ester derivatives of the following formulae:

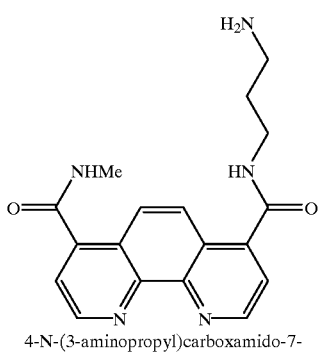
(3)
4-N-(3-aminopropyl)carboxamido-7-N-methylcarboxamido-1,10-phenanthroline

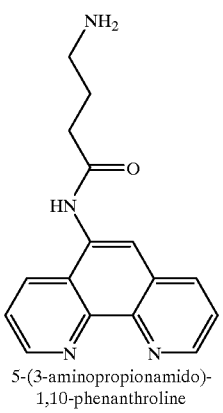
(6)
5-(3-aminopropionamido)-1,10-phenanthroline

Ligands of type Or" include at least one of:

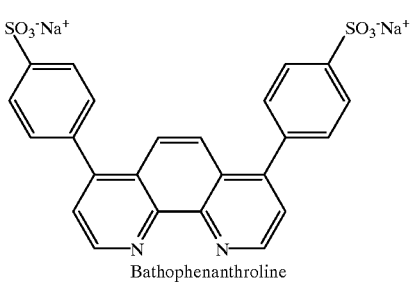
(1)
Bathophenanthroline

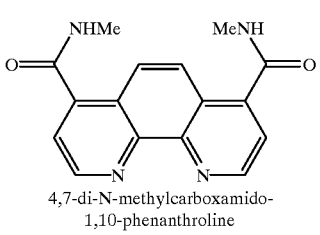
(2)
4,7-di-N-methylcarboxamido-1,10-phenanthroline (4)

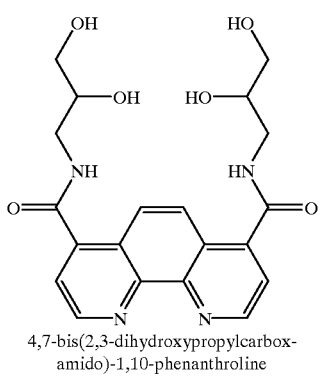

4,7-bis(2,3-dihydroxypropylcarbox-
amido)-1,10-phenanthroline (5)

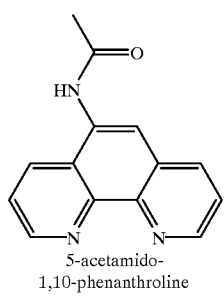

5-acetamido-
1,10-phenanthroline (i) From Platinum (II) acetate and substituted phenanthrolines: Platinum (II) acetate (34 mg, 0.1 mmol), and a mixture of ligands 3 and 2 in a ratio of approximately 2:7 (2 mg, 0.008 mmol) and ligand 4 (4 mg. 0.01 mmol) were stirred in N, N,-dimethylacetamide (DMA) (10 Ml) under a slow stream of nitrogen. The mixture was warmed to 60° C. to dissolve all the components, to give an orange-brown solution. After cooling to room temperature, one-half of a solution of sodium borohydride (3 mg) in DMA (6 Ml) was added slowly and carefully over a period of two hours to yield a dark black-brown solution. This was then stirred under a slow stream of air for 12 hours, then precipitated with diethyl ether and filtered on a medium porosity glass frit packed with diatomaceous earth. The resulting brown-black solid was extracted into ethanol/water, evaporated to dryness, then dissolved in DMSO (0.5 Ml) and 0.6 M triethylammonium bicarbonate in 20% isopropanol/water (1.0 Ml) and separated from smaller molecules on a coarse gel filtration column (GH25, Amicon) eluted with 0.6 M triethylammonium bicarbonate in 20% isopropanol/water. The cluster was the first species eluted, in the exclusion volume.

(ii) From Platinum (II) acetate, bathophenanthroline and 4,7-disubstituted phenanthrolines: Platinum (II) acetate (67 mg, 0.2 mmol), and a mixture of ligands 3 and 2 in a ratio of approximately 2:7 (3.5 mg, 0.012 mmol) and ligand 1 (12 mg. 0.02 mmol) were stirred in N, N,-dimethylacetamide (DMA) (15 Ml) under a slow stream of nitrogen to give an orange-brown solution. After cooling to room temperature, one-half of a solution of sodium borohydride (6 mg) in DMA (6 Ml) was added slowly and carefully over a period of two hours and 30 minutes to yield a dark black-brown solution. This was then stirred under a slow stream of air for 12 hours, then precipitated with diethyl ether and filtered on a medium porosity glass frit packed with diatomaceous earth. The resulting brown-black solid was extracted into ethanol/water, evaporated to dryness, then dissolved in DMSO (0.5 Ml) and 0.6 M triethylammonium bicarbonate in 20% isopropanol/water (1.0 Ml) and separated from smaller molecules by gel filtration chromatography as described above.

(iii) From platinum (II) acetate and 5-substituted 1,10-phenanthrolines: Platinum (II) acetate (34 mg, 0.1 mmol), and a mixture of ligands 5 (3.9 mg, 0.015 mmol) and 6 (1.5 mg, 0.005 mmol) were stirred in N, N,-dimethylacetamide (8 Ml) under a slow stream of nitrogen. The mixture was warmed to 80° C. to dissolve all the components, then cooled to room temperature. A solution of sodium borohydride (1.5 mg) in DMA (3 Ml) was added slowly and carefully over a period of one hour to yield a dark black-brown solution. This was precipitated with diethyl ether, stirred under air for 4 hours, then filtered on a pad of diatomaceous earth in a medium porosity glass frit. The resulting brown-black solid was extracted into 0.6 M triethylammonium bicarbonate in 20% isopropanol/water, evaporated to dryness, then dissolved in DMSO (0.5 Ml) and 0.6 M triethylammonium bicarbonate in 20% isopropanol/water (1.0 Ml) and separated from smaller molecules on a coarse gel filtration column (GH25, Amicon) eluted with 0.6 M triethylammonium bicarbonate in 20% isopropanol/water as described above.

(iv) From platinum (II) acetylacetonate and bathophenanthroline: A mixture of platinum (II) acetylacetonate (0.20 g, 0.5 mmol), bathophenanthroline (1:35 mg, 0.064 mmol) and a mixture of ligands 3 and 2 in a ratio of approximately 2:7 (5 mg, 0.016 mmol) was stirred in glacial acetic acid (20 Ml) under a slow flow of nitrogen. Meanwhile sodium borohydride (2.3 g) was dissolved in 2-methoxyethyl ether (diglyme: 30 Ml) and a 1:1 mixture of ethanol/water (20 Ml) was added dropwise over 30 mins; the hydrogen generated from this solution was bubbled into the reaction mixture. After 30 mins no color change was observed: therefore a small amount of platinum (II) chloride (~0.05 g) suspended in acetic acid (1 Ml) was added and stirring continued. $H_2$ bubbling was continued for a further 4 h, during which time the solution darkened from yellow to green and a greenish-black precipitate was formed. The solution was then aerated for 2 h by blowing air into the flask.

The contents of the reaction vessel were evaporated to dryness, and the greenish-black solid extracted with DMSO (0.5 Ml) and 0.6 M triethylammonium bicarbonate in 20% isopropanol/water (1.5 Ml), filtered, then separated over a coarse gel filtration column (GH25, Amicon) eluting with 0.6 M triethylammonium bicarbonate in 20% iso-propanol/water. A dark greenish-brown compound was eluted in the void volume, and pale yellow species later.

(v) From Platinum (II) chloride and substituted phenanthrolines: A mixture of platinum (II) chloride (0.5 mmol, 126 mg), ligands 2 (14.8 mg) and 3 (5.1 mg) were stirred in glacial acetic acid (25 Ml) for 6 h and heated to 100° C. to partially dissolve the solids. After cooling to room temperature overnight, hydrogen generated as described above) was bubbled slowly through the reaction mixture for 3 h; the color darkened from brown to greenish-black. The reaction mixture was then poured into a glass beaker and stirred overnight while air was bubbled through the solution. All the acetic acid was removed to leave a greenish-black solid. This was then extracted into DMSO (0.5 Ml) and 0.6 M triethylammonium bicarbonate in 20% DMSO/water (1.5 Ml), filtered, and separated on a coarse gel filtration column (GH25, Amicon) eluting with 0.6 M triethylammonium bicarbonate in 20% DMSO/water. A brownish-green species was eluted in the void volume.

14. Conjugation of Platinum Cluster to Antibodies

F(ab')$_2$ fragments or IgG molecules were reduced with 40 or 50 Mm respectively mercaptoethylamine hydrochloride in 0.1 M sodium phosphate buffer with 5 Mm EDTA, Ph 6.0, for 1 h 5 mins at room temperature (in 1.5 Ml volume). Reduced antibody was separated from excess mercaptoethylamine hydrochloride on a coarse gel filtration column (GH25, Amicon), eluting with 0.02 m sodium phosphate with 150 Mm sodium chloride and 1 Mm EDTA, Ph 6.5; reduced antibody was eluted in the excluded volume.

(i) Using sulfo-SMCC; (4-maleimido-1-Sulfo-cyclohexanecarboxylate): 1.8 to 3.6 nm Platinum cluster (as isolated above; equivalent to about one-third of the yield from 67 mg platinum (II) acetate) was evaporated to dryness, then re-evaporated to dryness five times from methanol solution to remove triethylammonium bicarbonate. The compound was then dissolved in DMSO (0.20 Ml) and 0.1 m HEPES-sodium hydroxide, Ph 7.5 (0.36 Ml), and added to a solution of 4-maleimido-1-Sulfo-cyclohexanecarboxylate (Sulfo-SMCC: 6 mg) in DMSO (0.04 Ml); the solution was mixed thoroughly, then stirred gently (rotary shaker) for 1 h 30, mins at room temperature. The activated platinum compound was then separated from excess smaller molecules on a coarse gel filtration column (GH25, Amicon), eluting with 0.02 m sodium phosphate with 150 Mm NaCl and 1 Mm EDTA in 20% DMSO/water; platinum-containing fractions were then added to those containing approximately 0.5 mg of reduced antibody Fab' fragments or IgG molecules, mixed thoroughly, and the mixture was incubated at 4° C. overnight.

Next day, the reaction mixture was concentrated to between 0.3 and 0.8 Ml by membrane centrifugation (Centricon-30) and the products separated on a size fractionation column (Pharmacia Superose-12) eluted with 0.02 m sodium phosphate with 150 Mm sodium chloride, Ph 7.4; the first species to be eluted was greenish-brown in color eluted with a retention time usually observed for antibody molecules and conjugates. In the Fab' preparations, fractions comprising this peak were concentrated and re-chromatographed on a Superdex-75 column in the same buffer. The first species to emerge was the antibody conjugate.

(ii) Using N-methoxy carbonyl maleimide: 1.8 to 3.6 nm platinum cluster (as isolated above; equivalent to about one-third of the yield from 67 mg platinum (II) acetate) was evaporated to dryness, then re-evaporated to dryness five times from methanol solution to remove triethylammonium bicarbonate. The compound was then dissolved in DMSO (0.25 Ml) and 0.1 m sodium phosphate, Ph 7.5 (0.48 Ml), and added to a solution of N-methoxycarbonylmaleimide (NMCM: 6 mg in DMSO (0.07 Ml); the solution was mixed thoroughly and incubated at 0° C. (ice bath/refrigerator) for 30 mins. The activated platinum compound was then separated from excess smaller molecules on a coarse gel filtration column (GH25, Amicon), eluting with 0.02 m sodium phosphate with 150 Mm NaCl and 1 Mm EDTA in 20% DMSO/water. Antibody labeling and isolation were conducted identical to those described for other platinum cluster conjugates described above.

15. Preparation of Functionalized 2.4–3.6 nm Palladium Cluster (i) From palladium (II) acetate by reduction with sodium borohydride: Palladium (II) acetate (45 mg, 0.2 mmol), and a mixture of ligands 3 and 2 in a ratio of approximately 2:7 (7.5 mg, 0.025 mmol) were stirred in N,N,-dimethylacetamide (DMA) (15 Ml) under a slow stream of nitrogen. The mixture was warmed to 80° C. to dissolve all the components, to give an orange-brown solution. After cooling to room temperature, a solution of sodium borohydride (3 mg) in DMA (6 Ml) was added slowly and carefully over a period of two hours to yield a dark black-brown solution. This was stirred in a glass beaker under a stream of air for 12 hours, then precipitated with diethyl ether, filtered on a pad of diatomaceous earth in a glass frit, extracted into ethanol/water and evaporated to dryness. The solid was dissolved in DMSO (1.0 Ml) and 0.6 M triethylammonium bicarbonate in 20% DMSO/water (3.0 Ml), filtered, and separated on a coarse gel filtration column (GH25, Amicon) eluting with 0.6 M triethylammonium bicarbonate in 20% DMSO/water. The cluster was eluted in the exclusion volume.

(ii) From palladium (II) acetate by reduction with sodium borohydride: Palladium (II) acetate (45 mg, 0.2 mmol), and a mixture of ligands 3 and 2 in a ratio of approximately 2:7 (4.5 mg, 0.015 mmol) and ligand 1 (6 mg, 0.01 mmol) were stirred in a mixture of benzene (4 Ml), ethanol (5 Ml), water (5 Ml) and dichloromethane (5 Ml) under a slow stream of nitrogen. A solution of sodium borohydride (6 mg) in ethanol (5 Ml) was added slowly over a period of one hour to yield a dark black-brown solution. This was stirred in a glass beaker under a stream of air until dry, then dissolved in DMSO (1.0 Ml) and 0.6 M triethylammonium bicarbonate in 20% DMSO/water (3.0 Ml), filtered, and separated on a coarse gel filtration column (GH25, Amicon) eluting with 0.6 M triethylammonium bicarbonate in 20% DMSO/water. The cluster was eluted in the exclusion volume.

(iii) From palladium (II) acetate by reduction with hydrogen: Palladium (II) acetate (1.0 mmol, 227 mg), and a mixture of ligands 2 (27 mg) and 3 (8.5 mg) were stirred in glacial acetic acid (25 Ml) with stirring under a slow stream of nitrogen. The mixture was warmed to 80° C. to dissolve all the components, to give an orange-brown solution. After cooling to room temperature hydrogen (generated by the addition of water/ethanol to sodium borohydride in diglyme as described above) was bubbled slowly through the mixture for 3 h to give a near-black solution. This was stirred in a glass beaker under a stream of air until dry, then dissolved in DMSO (1.0 Ml) and 0.6 M triethylammonium bicarbonate in 20% DMSO/water (3.0 Ml), filtered, and separated on a coarse gel filtration column (GH25, Amicon) eluting with 0.6 M triethylammonium bicarbonate in 20% DMSO/water. The cluster was eluted in the exclusion volume.

16. Conjugation of Palladium Cluster to Antibodies

Fab' and IgG conjugation were conducted using the same procedure used with the platinum cluster: IgG or F(ab')$_2$ was first reduced with mercaptoethylamine hydrochloride and separated from excess reducing agent as previously described.

(ii) Cluster activation with sulfo-SMCC (4-maleimido-1-Sulfo-cyclohexane-carboxylate): Palladium clusters (about one-third of the yield from 0.224 g of palladium (II) acetate) was evaporated to dryness five times from methanol to remove triethylammonium bicarbonate. The brown-black solid was dissolved in DMSO (0.32 Ml) and 0.1 M HEPES-sodium hydroxide buffer at Ph 7.50 (0.50 Ml) and added to a solution of (4maleimido-1-Sulfo-cyclohexane-carboxylate (Sulfo-SMCC: 12 mg) in DMSO (0.08 Ml). The mixture gently at room temperature for 1 hour 20 minutes, then separated by gel filtration on a coarse gel column (GH25, Amicon). The activated cluster was eluted in the void volume; cluster-containing fractions were pooled and added to the reduced antibody. Sufficient activated cluster was produced to label 0.5 mg of Fab' fragments and 0.75 mg of IgG molecules. The mixture was left at room temperature for 1 h, then incubated at 4° C. (refrigerator) overnight.

Next day, the reaction mixture was concentrated to between 0.3 and 0.8 Ml by membrane centrifugation (Centricon-30) and the products separated on a size fractionation column (Pharmacia Superose-12) eluted with 0.02 m sodium phosphate with 150 Mm sodium chloride, Ph 7.4; the first species to be eluted was greenish-brown in color eluted with a retention time usually observed for antibody molecules and conjugates. In the Fab' preparations, fractions comprising this peak were concentrated and re-chromatographed on a Superdex-75 column in the same buffer. The first species to emerge was the antibody conjugate.

(ii) Cluster activation with N-methoxycarbonylmaleimide: A suitable amount of the cluster was evaporated to dryness five times from methanol to remove triethylammonium bicarbonate. The brown-black solid was dissolved in DMSO (0.32 Ml) and 0.1 M sodium phosphate, Ph 7.50 (0.40 Ml) and added to a solution of N-methoxycarbonylmaleimide (NMCM: 6 mg) in DMSO (0.05 Ml). The mixture is vortexed, incubated at 0° C. for 30 minutes (ice bath/refrigerator) then separated on a GH25 column. The activated cluster is eluted in the void volume; cluster-containing fractions are pooled and added to 0.5 mg of Fab' fragments or to 0.8 mg of reduced IgG molecules. The mixture is left at room temperature for 1 h, then incubated at 4° C. overnight. Antibody conjugates were isolated as described for the platinum clusters.

17. Conjugation of Functionalized Platinum Cluster to Antibodies

F(ab')$_2$ fragments or IgG molecules were reduced with 40 or 50 mM respectively mercaptoethylamine hydrochloride in 0.1 M sodium phosphate buffer with 5 mM EDTA, pH 6.0, for 1 hour and 5 minutes at room temperature (in 1.5 mL volume). Reduced antibody was separated from excess mercaptoethylamine hydrochloride on a coarse gel filtration column (GH25, Amicon), eluting with 0.02 m sodium phosphate with 150 Mm sodium chloride and 1 Mm EDTA, Ph 6.5; reduced antibody was eluted in the excluded volume.

Platinum cluster (as isolated above; approximately one-third of the total isolated) was evaporated to dryness, then re-evaporated to dryness five times from methanol solution to remove triethylammonium bicarbonate. The compound was then dissolved in DMSO (0.25 Ml) and 0.1 m sodium phosphate, Ph 7.5 (0.48 Ml), and added to a solution of N-methoxycarbonylmaleimide (NMCM: 6 mg) in DMSO (0.07 Ml); the solution was mixed thoroughly and incubated at 0° C. (ice bath/refrigerator) for 30 minutes. The activated platinum compound was then separated from excess smaller molecules on a coarse gel filtration column (GH25, Amicon), eluting with 0.02 m sodium phosphate with 150 Mm NaCl and 1 Mm EDTA in 20% DMSO/water; platinum-containing fractions were then added to those containing reduced antibody, mixed thoroughly and the mixture was incubated at 4° C. overnight.

Next day, the reaction mixture was concentrated to between 0.5 and 1 Ml (Centricon-30) and the products separated on a size fractionation column (Pharmacia Superose-12) eluted with 0.02 m sodium phosphate with 150 Mm sodium chloride, Ph 7.4; the first species to be eluted was greenish-brown in color and was in the position expected for antibody molecules. In the Fab' preparations, fractions comprising this peak were concentrated and re-chromatographed on a Superdex-75 column in the same buffer. The first species to emerge was the antibody conjugate; some resolution of unlabeled from labeled Fab' fragments was observed.

18. Preparation and Antibody Conjugation of Functionalized 2–3 nm Pd Cluster

Fab' conjugation is conducted using the same procedure used with the platinum cluster: F(ab')$_2$ is first reduced and separated from excess reducing agent in the same manner. A suitable amount of the cluster is evaporated to dryness three times from methanol, with heating to 55–60° C. to remove DMSO. The black solid is dissolved in DMSO (0.32 Ml) and 0.1 M sodium phosphate, Ph 7.50 (0.40 Ml) and added to a solution of N-methoxycarbonylmaleimide NMCM: 6 mg) in DMSO (0.05 Ml). The mixture is vortexed, incubated at 0° C. for 30 minutes (ice bath/refrigerator) then separated on a GH25 column. The activated cluster is eluted in the void volume: cluster-containing fractions are pooled and added to the reduced antibody. The mixture is left at room temperature for 1 hour, then stored at 4° C. overnight.

19. Immunoblotting of Conjugates

Immunoblotting was conducted using a single-layer technique: mouse IgG was spotted onto a hydrated nitrocellulose membrane in serial dilutions, and detected using platinum or palladium labeled goat IgG and Fab' anti-mouse IgG conjugates.

Buffers Required:
PBS: 0.01 M sodium phosphate with 150 mm sodium Chloride, Ph 7.4
Wash:
    0.02 M sodium phosphate with 150 mm sodium chloride, Ph 7.4
    0.8% w/w bovine serum albumin, fraction V by heat shock.
    0.1% w/w gelatin, type B from bovine skin, approximately 60 bloom
    2 Mm sodium azide.
Blocking:
    0.02 M sodium phosphate with 150 mm sodium chloride, Ph 7.4
    4.0% w/w bovine serum albumin, fraction V by heat shock.
    0.1% w/w gelatin, type B from bovine skin, approximately 60 bloom 2 Mm sodium azide.
Incubation:
    0.02 M sodium phosphate with 150 mm sodium chloride, Ph 7.4 0.8%
    w/w bovine serum albumin, fraction V by heat shock.
    0.1% w/w gelatin, type B from bovine skin, approx. 60 bloom
    1% W/W normal goat serum 2 Mm sodium azide.
Procedure:
1. A nitrocellulose membrane, marked with pencilled divisions for antigen concentration identification, was simmered in gently boiling water for minutes.
2. 1 $\mu$l dilutions of mouse IgG were spotted onto membrane, from $10^{-9}$ g to $10^{-18}$ g.
3. Membrane was blocked with blocking buffer for 30 minutes at 45° C.
4. Membrane washed 5 minutes with wash buffer.
5. Membrane was incubated with 5 Ml of a 1/200 dilution of a 0.08 mg/Ml solution of one of Pd, Pt duster conjugate in incubation buffer for 2.5 hours at room temperature, with slow agitation.
6. Membrane was rinsed with buffer 3 (3×5 mins), then PBS (3×30 seconds).
7. Membrane postfixed with glutaraldehyde, 1% in PBS (10 minutes).
8. Rinsed with deionized water (2×5 minutes).
9. Rinse with 0.05 M EDTA at Ph 4.5 (2 minutes).
10. Develop with freshly mixed LI SILVER™ Nanoprobes, Inc.), 2×30 minutes. Rinse thoroughly with deionized water between developments to remove all the silver enhancement reagent.

11. Rinse repeatedly with deionized water, then let air-dry.

The last visible spot in a series of decreasing concentration contained 10 pg of mouse IgG for platinum-labeled goat Fab'- and IgG-anti-mouse IgG, and also for palladium-labeled goat anti-mouse Fab'. For the IgG conjugates, this was the same level of sensitivity as was obtained from a second blot performed with the analogous Nanogold conjugate.

Thiol-Gold Cluster Preparation and Antibody Labelling Procedure

The following solutions are used in the preparation of thiol-gold clusters:

A. $NaBH_4$ solution: 0.2% solution of $NaBH_4$ in ethanol.
B. TEAH: 0.6 M triethylammonium bicarbonate in distilled water.

Note: Unless otherwise specified, all reactions are performed at 25° C.

20. Synthesis of Thiol Gold Cluster from Aurothioglucose (I)

5 mg of aurothioglucose ($C_6H_{11}O_5SAu$) is dissolved in 0.5 ml of distilled $H_2O$ in a test tube, forming a light yellow solution. Two 10 μL aliquots of $NaBH_4$ solution are added to the aurothioglucose solution over 15 minutes. Upon $NaBH_4$ addition the solution turns dark brown in color. The cluster is purified by size exclusion chromatography using Amicon GH-25 material (MW cutoff=3000 Daltons), with TEAH as the elution buffer. The cluster is recovered from the void volume of the column. Cluster formation is verified by UV/VIS spectroscopy and electron microscopy.

21. Synthesis of Thiol Gold Cluster from $KAuBr_4$ and Glutathione (II)

5 mg of $Kaubr_4$ ($8.418\times10^{-3}$ mMol) is dissolved in 0.3 ml of distilled water. 5.17 mg of glutathione ($1.684\times10^{-2}$ mMol), dissolved in 0.5 ml of distilled water is added to the $Kaubr_4$ solution in two 0.25 ml aliquots at 5 minute intervals. After the first addition the dark reddish brown $Kaubr_4$ solution turns to a clear, colorless to pale yellow solution. The reaction, mixture is left for 5 minutes after the second addition of glutathione solution. The Ph of the reaction mixture is adjusted to 8 using 6 N NaOH solution. Two 10 μL aliquots of $NaBH_4$ solution are added to the reaction mixture over 15 minutes. The Ph is adjusted to neutral with 1 N Hcl solution, and a third 10 μL aliquot of $NaBH_4$ solution is added. Two 10 μL aliquot of $NaBH_4$ solution are added to the reaction mixture over 15 minutes. The Ph is adjusted to neutral with 1 N HCl solution, and a third 10 μL aliquot of $NaBH_4$ solution is added. Upon $NaBH_4$ addition the solution turns dark brown in color. The cluster is purified by size exclusion chromatography using Amicon GH-25 material (MW cutoff=3000 daltons), with TEAH as the elution buffer. The cluster is recovered from the void volume of the column. Cluster formation is verified by UV/VIS spectroscopy and electron microscopy.

22. Synthesis of a Mixed Thiol Gold Cluster from KAuBr4 and a Mixture of Glutathione and 1-thio-β-D-Glucose (III)

5 mg of $Kaubr_4$ ($8.418\times10^{-3}$ Mmol) is dissolved in 0.3 ml of distilled water. A mixed thiol solution of 3.62 mg of glutathione ($1.18\times10^{-2}$ Mmol) and 1.10 mg of 1-thio-β-Glucose ($5.05\times10^{-3}$ Mmol), dissolved in 0.5 ml of distilled water is added to the $Kaubr_4$ solution in two 0.25 ml aliquots at 5 minute intervals. After the first addition the dark reddish brown $KAuBr_4$ solution turns to a clear, colorless to pale yellow solution. The reaction mixture is left for 5 minutes after the second addition of the mixed thiol solution. The pH of the reaction mixture is adjusted to 8 using 6 N NaOH solution. Two 10 μL aliquots of $NaBH_4$ solution are added to the reaction mixture over 15 minutes. The pH is adjusted to neutral with 1 N HCl solution, and a third 10 μL aliquots of $NaBH_4$ solution is added. Upon $NaBH_4$ addition, the solution turns dark brown in color. The cluster is purified by size exclusion chromatography using Amicon GH-25 material (MW cutoff=3000 daltons), with TEAH as the elution buffer. The cluster is recovered from the void volume of the column. Cluster formation is verified by UV/VIS spectroscopy and electron microscopy.

23. Synthesis of antibodies (whole molecule) labelled with III:

2 mg of IgG is combined in a siliconized microcentrifuge tube with 10 mg of mercaptoethanolamine in 1.4 ml of 0.1 M sodium phosphate, Ph 6.0 which contains 5 Mm EDTA. The reaction is allowed to proceed 1 hour at room temperature, then the reduced antibody is separated from excess MEA on a GH-25 column (Amicon), eluting with 0.1 M borate buffer, Ph 9.2, with 5 Mm EDTA. The reduced antibody is collected in the void volume of the column. Fractions are combined and reduced in volume to 0.1 ml with centricon-30 (Amicon). The reduced antibody fraction is then incubated at 37° C. for 1 hour with a 20-fold excess of compound III, which is added in 0.1 M borate buffer, Ph 9.2, with 5 Mm EDTA. The total volume of this reaction mixture is made up to 1.4 ml by adding 0.1 M borate buffer, Ph 9.2, with 5 Mm EDTA. After incubation period, the reaction mixture is reduced in volume to 0.1 ml with centricon-30 (Amicon) and injected on a Superdex-75 molecular weight fractionation column (Pharmacia) to separate out the gold cluster-IgG conjugate from excess III. Antibody labelling is verified by UV/VIS spectroscopy and electron microscopy.

24. Synthesis of Fab' antibody fragments labelled with III:

2 mg of F(ab')$_2$ is combined in a siliconized microcentrifuge tube with 7 mg of mercaptoethanolamine in 1.4 ml of 0.1 M sodium phosphate, Ph 6.0 which contains 5 Mm EDTA. The reaction is allowed to proceed 1 hour at room temperature, then the reduced antibody fragment is separated from excess MEA on a GH-25 column (Amicon), eluting with 0.1 M borate buffer, Ph 0.2, with 5 Mm EDTA. The Fab' fragment is collected in the void volume of the column. Fractions are combined and reduced in volume to 0.1 ml with centricon-30 (Amicon). The Fab' fraction is then incubated at 37° C. for 1 hour with a 20-fold excess of III, which is added in 0.1 M borate buffer, Ph 9.2, with 5 Mm EDTA. The total volume of this reaction mixture is made up to 1.4 ml by adding 0.1 M borate buffer, pH 9.2, with 5 mM EDTA. After the incubation period, the reaction mixture is reduced in volume to 0.1 ml with centricon-30 (Amicon) and injected on a Superdex-75 molecular weight fractionation column (Pharmacia) to separate out the gold cluster-Fab' conjugate from excess III. Antibody labelling is verified by UV/VIS spectroscopy and electron microscopy.

Preparation of Thiol-Metal Clusters (Silver), Silver-gold, Platinum, Thallium)

25. Preparation of Silver-Organic Thiol Clusters $5\times10^{-6}$ moles of silver acetate in 0.5 ml of water was mixed with $1\times10^{-5}$ moles of thioglucose and heated to 70° C. for 5 minutes. Then $5\times10^{-6}$ moles of sodium borohydride was added. Later, $5\times10^{-6}$ moles of additional sodium borohydride was added. A dark brown solution resulted, and contained organo-silver clusters ~1–3 nm in diameter. These were purified by gel filtration size exclusion chromatography using an Amicon GH25 column (cutoff 3,000 MW) in an aqueous buffer of 0.6 M triethylammonium bicarbonate and 5% methanol. The product was rotary evaporated under vacuum and re-suspended in water. The size was assayed by electron microscopy.

26. Preparation of Mixed Silver-Gold Organic Thiol Clusters $2.5 \times 10^{-6}$ moles of silver acetate and $2.5 \times 10^{-6}$ moles of chloroauric acid in 0.5 ml of water were mixed with $1 \times 10^{-5}$ moles of thioglucose. Then, $5 \times 10^{-6}$ moles of sodium borohydride was added. A dark brown solution resulted, and contained organo-silver/gold clusters ~1–3 nm in diameter. These were purified by gel filtration size exclusion chromatography using an Amicon GH25 column (cutoff 3,000 MW) in an aqueous buffer of 0.6 M triethylammonium bicarbonate and 5% methanol. The product was rotary evaporated under vacuum and resuspended in water. The size was assayed by electron microscopy.

27. Preparation of Platinum-Organic Thiol Clusters $5 \times 10^{-6}$ moles of platinum chloride in 0.5 ml of water was mixed with $5 \times 10^{-6}$ moles of thioglucose and heated to 60° C. for 5 minutes. Then $2.5 \times 10^{-6}$ moles of sodium borohydride was added. Later, $2.5 \times 10^{-6}$ moles of additional sodium borohydride was added. A dark brown solution resulted, and contained organo-platinum clusters ~1–3 nm in diameter. These were purified by gel filtration size exclusion chromatography using an Amicon GH25 column (cutoff 3,000 MW) in an aqueous buffer of 0.6 M triethylammonium bicarbonate and 5% methanol. The product was rotary evaporated under vacuum and re-suspended in water. The size was assayed by electron microscopy.

28. Preparation of Thallium-Organic Thiol Clusters $5 \times 10^{-6}$ moles of thallium chloride in 0.5 ml of water was mixed with $1 \times 10^{-5}$ moles of thioglucose. After 10 minutes, $5 \times 10^{-6}$ moles of sodium borohydride was added. Later, $2.5 \times 10^{-6}$ moles of additional sodium borohydride was added. A dark brown solution resulted, and contained organo-thallium clusters ~1–3 nm in diameter. These were purified by gel filtration size exclusion chromatography using an Amicon GH25 column (cutoff 3,000 MW) in an aqueous buffer of 0.6 M triethylammonium bicarbonate and 5% methanol. The product was rotary evaporated under vacuum and re-suspended in water. The size was assayed by electron microscopy.

Thiol-Gold Clusters for Protein Staining in Polyacrylamide Gel Electrophoresis (PAGE): Preparation and Application The following solutions are used in the preparation of thiol-gold clusters:

A. $NaBH_4$ solution: 0.2% solution of $NaBH_4$ in ethanol.

B. TEAH: 0.6 M triethylammonium bicarbonate in distilled water.

Note: Unless otherwise specified, all reactions arm performed at 25° C.

29. Synthesis of Thiol-gold Cluster from $KAuBr_4$ and o-mercaptobenzoic Acid (I)

5 mg of KAuBr4 ($8.41 \times 10^{-3}$ mMol) is dissolved in 0.3 ml of distilled water. 2.60 mg of o-mercaptobenzoic acid ($1.68 \times 10^{-2}$ mMol), dissolved in 0.5 ml of TEAH is added to the $KAuBr_4$ solution in two 0.25 ml aliquots at 5 minute intervals. After the first addition, the dark reddish brown $KAuBr_4$ solution turns to clear, colorless to pale yellow solution. The reaction mixture is left for 5 minutes after the second addition of glutathione solution. Two 10 μL aliquots of $NaBH_4$ solution are added to the reaction mixture over 15 minutes. Upon $NaBH_4$ addition the solution turns dark brown in color. The duster is purified by size exclusion chromatography using Amicon GH25 material (MW cutoff= 3000 daltons), with TEAH as the elution buffer. The cluster is recovered from the void volume of the column. The cluster containing fractions are combined in a 50 ml round bottom flask and the solution is evaporated to dryness with a rotoevaporator (Buchi). The cluster is redissolved in methanol and re-evaporated with the rotoevaporator. This methanol evaporation is done 5 times. The cluster is then dissolved in 0.1 sodium phosphate buffer, pH 8.0, with 1.0 mM EDTA for use in subsequent protein staining experiments. Cluster formation is verified by UV/VIS spectroscopy and electron microscopy. As a thiol scavenger, an excess amount of N-ethylmaleimide is added to the cluster solution.

30. Synthesis of a Mixed Thiol Gold Cluster from $Kaubr_4$ and Mixture of o-mercaptobenzoic Acid and Nonylmercaptan(II)

5 mg of $Kaubr_4$ ($8.41 \times 10^{-3}$ Mmol) is dissolved in 0.3 ml of 90% ethanol in distilled $H_2O$. A mixed thiol solution of 2.34 mg of o-mercaptobenzoic acid ($1.52 \times 10^{-2}$ Mmol) and 0.27 mg of nonylmercaptan ($1.68 \times 10^{-3}$ Mmol), dissolved in 0.5 ml of 95% ethanol in 6N NaOH, is added to the $Kaubr_4$ solution in two 0.25 ml aliquots at 5 minute intervals. After the first addition, the dark reddish brown $Kaubr_4$ solution turns to a pale yellow precipitate. Upon the addition of the second thiol mixture addition, the precipitate is solubilized to give a clear, colorless to pale yellow solution. The reaction mixture is left for 5 minutes after the second addition of the mixed thiol solution. Two 10 μL aliquots of $NaBH_4$ solution are added to the reaction mixture over 15 minutes. The Ph is adjusted to neutral with 1 N Hcl solution, and a third 10 μL aliquots of $NaBH_4$ solution is added. Upon $NaBH_4$ addition, the solution turns dark brown in color. The cluster is purified by size exclusion chromatography using Amicon GH-25 material (MW cutoff=3000 Daltons), with TEAH as the elution buffer. The cluster is recovered from the void volume of the column. The cluster containing fractions are combined in a 50 ml round bottom flask and the solution is evaporated to dryness with a rotoevaporator (Buchi). The cluster is redissolved in methanol and re-evaporated with the rotoevaporator. This methanol evaporation is done 5 times. The cluster is then dissolved in 0.1 sodium phosphate buffer, Ph 8.0, with 1.0 Mm EDTA for use in subsequent protein staining experiments. Cluster formation is verified by UV/VIS spectroscopy and electron microscopy. As a thiol scavenger, an excess amount of N-ethylmaleimide is added to the cluster solution.

31. Application of I and II to SDS-PAGE in Non-reducing Conditions

Protein sample (Pharmacia LMW calibration kit proteins) to be analyzed is incubated with excess I or II in 10 Mm Tris/Hcl, 1 mM EDTA, Ph 8.0. To the sample is added Sodium Dodecyl Sulphate (SDS) to 2.5%. The sample is heated for 5 minutes at 100° C. Bromophenol Blue is added to 0.01%. Using an eight "well" sample applicator, eight 1 μL aliquots of the sample mixture are applied to a Phastgel gradient gel (8–25) and run on the Pharmacia Phastgel system using the following protocol:

| | | | | | |
|---|---|---|---|---|---|
| Sample Applicator down at step 1.1 | | | | 1 Vh | |
| Sample Applicator up at step 1.1 | | | | 10 Vh | |
| SEP 1.1 | 250 V | 10.0 mA | 3.0 W | 15° C. | 65 Vh |
| SEP 1.2 | 50 V | 0.1 mA | 0.5 W | 15° C. | 0 Vh |

After electrophoresis, the gel is developed for 5–15 minutes (or until background development) with U SILVER enhancement kit (Nanoprobes, Inc.). After silver development, gels are rinsed thoroughly with deionized water, and preserved by incubation in 20% glycerol in deionized water at 45° C. for 10 minutes.

32. Application of I and II to SDS-PAGE in reducing conditions:

Protein sample (Pharmacia LMW calibration kit proteins) to be analyzed is incubated with a 2.5% mercaptosuccinic acid solution in 10 Mm Tris/Hcl, 1 mM EDTA, Ph 8.0. To the sample is added Sodium Dodecyl Sulphate (SDS) to 2.5%. The sample is heated for 5 minutes at 100° C. Bromophenol Blue is added to 0.01% and N-ethylmaleimide (prepared as a 20% solution in DMSO) is added to 5%. The sample is incubated at room temperature for 10 minutes. Excess amounts of I and II are added to the sample mixture. Using an eight well sample applicator, eight 1 $\mu$L aliquots of the sample mixture are applied to a Phastgel gradient gel (8–25) and run on the Pharmacia Phastgel system using the following protocol:

| Sample Applicator down at step 1.1 | | | | 1 Vh | |
|---|---|---|---|---|---|
| Sample Applicator up at step 1.1 | | | | 10 Vh | |
| SEP 1.1 | 250 V | 10.0 mA | 3.0 W | 15° C. | 65 Vh |
| SEP 1.2 | 50 V | 0.1 mA | 0.5 W | 15° C. | 0 Vh |

After electrophoresis, the gel is developed for 5–15 minutes (or until ba round development) with LI SILVER enhancement kit (Nanoprobes, Inc.). After silver development, gels are rinsed thoroughly with deionized water, and preserved by incubation in 20% glycerol in deionized water at 45° C. for 10 minutes.

Nucleic Acid
Detection of Oligonucleotides

General: Oligonucleotides modified to contain biotin can be detected through the use of either gold cluster labeled anti-biotin antibodies, antibody fragments, gold cluster-labeled streptavidin, or gold cluster-labeled avidin. Incorporation of the biotin into an oligonucleotide strand can occur via a commercially available biotin-NHS reagent and a primary amine that was introduced onto the oligonucleotide via a modified nucleotide or nucleotide substitute (phosphoramidite) by a DNA synthesizer. The biotin labeled oligonucleotide can then be reacted with gold cluster labeled reagent designed to react with the biotin moiety and observed via silver development.

33. An oligonucleotide having a primary amine attached to the 5' end was reacted in sightly alkaine sodium phosphate buffer with a large molar excess of biotin-LC-N-hydroxysuceinimide ester (biotin-LC-NHS II; Pierce) dissolved in DMSO. After 1 hour at room temperature the reaction mixture was purified on a GH25 (nominal exclusion limit 3000 D) column and fractions measured for nucleic acid content by monitoring at 260 nm. By comparing the ratio of the 260 and 240 nm peaks to gauge biotin incorporation. Recovered nucleic acid yield 49%.

The biotin labeled oligonucleotides were reacted with streptavidin gold cluster conjugates in phosphate buffered saline (PBS), Ph 7.4 for four hours at room temperature and separated by size exclusion chromatography (Superdex 75, nominal exclusion limit 70 kD) using the same buffer as eluant. On this column, the major peaks coincided with the retention time of the cluster conjugate and showed enhanced absorption at 260 nm indicating reaction had occurred.

34. Detection of Biotinylated DNA: Dot Blots

Blot tests were conducted to test the incorporation of gold in the isolated product. In a typical run, biotin labeled oligonucleotides was serially diluted in water by factors of ten starting a $2.5 \times 10^{-7}$ M solution and ending at $2.5 \times 10^{-16}$ M. 1 $\mu$L spots were applied to a nitrocellulose membrane by Drummond capillary pipettes. The membrane was allowed to dry and then subjected to a 302 nm light placed 18 cm from the membrane for ten minutes. The membrane was blocked with 4% bovine serum albumin (BSA) for 30 minutes at 37° C. The membrane was then incubated with the streptavidin gold cluster conjugate diluted to about 2 $\mu$g/ml in 0.8% BSA for 1.5 hours. After rinsing with buffer and then water, the membrane was treated with silver developer. The membrane was again rinsed with water and examined for spot generation after drying. The silver developed gold particle is seen as a dark spot. The spots appearing unambiguously above background provide a limit of detection on the order of 10 to 100 attomole (1 attomol=$10^{-18}$ mol) detected with more concentrated applications appearing darker than dilute ones.

35. Preparation and Detection of Biotinylated M13mp18

Another model system was the preparation of labeled complementary fragments to the single stranded phage M13mp18. Using the random primer method, biotin was introduced as modified dUTP and incorporated with Klenow. After purification using GeneClean, the biotinylated solution was applied to a nitrocellulose membrane, immobilized in a vacuum oven and detected by streptavidin gold cluster conjugate. In this procedure $10^{-15}$ mol M13mp18 was detected. The detection limit was independent of the concentration of the gold conjugate.

Preparation of Gold Cluster Labeled DNA Hybridization Probes

36. Random Primer Extension Method

Gold cluster labelled nucleotide triphosphate was prepared by reaction of NHS-gold cluster with an amino modified nucleotide triphosphate. Example: Amino-7-DUTP, available from Clontech, is a DUTP analog with a primary amine covalently attached to the pyrimidine ring through a seven atom spacer arm. 50 nmol Amino-7-DUTP was reacted with 5 nmol mono-N-hydroxysulfosuccinimide-1.4 nm gold cluster in 20 Mn HEPES-NaOH buffer Ph 7.5 at 4° C. overnight. The reaction mixture was separated on a GH25 column to remove unreacted nucleotide form the conjugate. The product was further purified by ion exchange chromatography over TSK DEAE with elution at 0.3M triethylammonium hydrogencarbonate.

The modified nucleotide was incorporated into an oligonucleotide by enzymatic extension of random primers.

Preparation of Large Platinum and Palladium Cluster-Lipid Conjugates

The cluster complexes used to prepare the lipid conjugates described in this section were prepared using the following ligands:

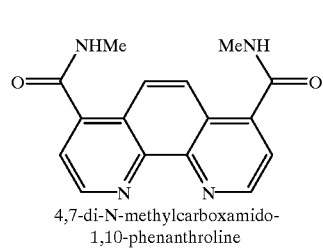

(1)

4,7-di-N-methylcarboxamido-1,10-phenanthroline (2)

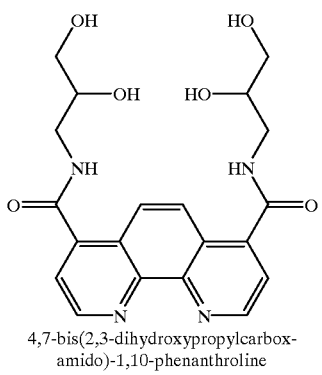

4,7-bis(2,3-dihydroxypropylcarbox-
amido)-1,10-phenanthroline (3)

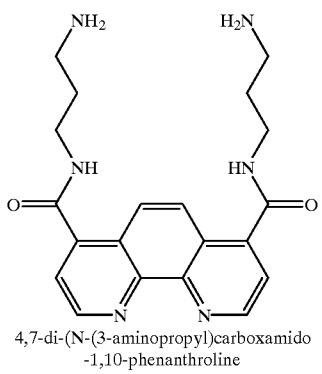

4,7-di-(N-(3-aminopropyl)carboxamido
-1,10-phenanthroline (4)

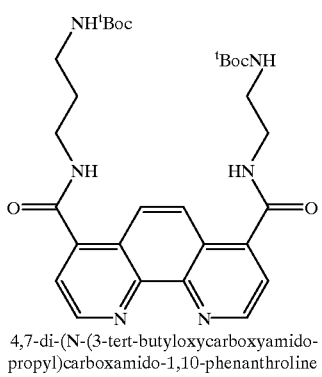

4,7-di-(N-(3-tert-butyloxycarboxyamido-
propyl)carboxamido-1,10-phenanthroline (5)

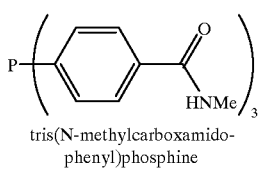

tris(N-methylcarboxamido-
phenyl)phosphine (6)

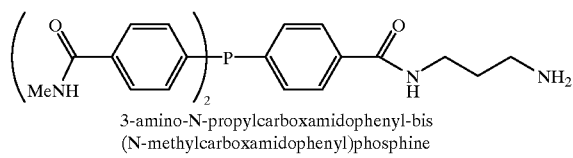

3-amino-N-propylcarboxamidophenyl-bis
(N-methylcarboxamidophenyl)phosphine

Preparation of 2–3 nm Platinum Cluster

Platinum (II) acetate (64 mg, 0.2mmol), and a mixture of ligands 1 and 4 in a ratio of approximately 10:1 (15 mg, 0.0455 nmol of 1, and 3 mg, 0.00455 nmol of 4) were stirred in N, N-dimethylacetamide (DMA, 20 mL) under a slow stream of nitrogen. The mixture was warmed to −60° C. to dissolve all the components, to give an orange-brown solution. After cooling to room temperature, a solution of sodium borohydride (7.6 mg, 0.2 nmol) in DMA (6 mL) was added dropwise over 15 minutes to yield a dark black-brown solution. After stirring for 16 h, the stoppers were removed and air was first blown into the flask (3 h) then bubbled through the solution (2 h). The dark brown product was then precipitated with diethyl ether (100 mL), filtered on a medium porosity glass frit packed with diatomaceous earth, then redissolved in 0.6 M triethylammonium bicarbonate in 20% isopropanol/water (1:5 mL). The large cluster was separated from smaller species by gel filtration over a coarse gel (GH25, Amicon) eluted with the same buffer. Fractions containing the dark brown cluster (species eluted first) were combined.

Half of this material was evaporated to dryness, then evaporated to dryness a further five times from methanol solution, then redissolved in 2.5 mL methanol and 83 μL of hydrochloric acid (2N in water) was added and the mixture stirred for 30 minutes to remove the t-Boc groups (converting ligand 4 to ligand 3). 2 mL of 0.6 M triethylammonium bicarbonate in 20% isopropanol/water was added, the mixture evaporated to dryness and the deprotected cluster was isolated by gel filtration over a coarse gel (GH25, Amicon) eluted with the same buffer.

Preparation of 2–3 nm Palladium Cluster

Preparation followed that of the analogous platinum cluster. Palladium (II) acetate (45 mg, 0.2 nmol), ligands 1 (15 mg, 0.0455 nmol) and ligand 4 (0.00455 nmol) were dissolved in DMA (20 mL) under nitrogen at −60° C., cooled to room temperature, and reduced with a solution of sodium borohydride (7.6 mg, 0.2 nmol) in DMA (6 mL) added dropwise over 15 minutes to yield a dark brown solution. After stirring for 16 h, the stoppers were removed and air was blown into the flask (3 h) then bubbled through the solution (2 h). The product was precipitated with diethyl ether (100 mL), filtered (medium porosity glass frit/ diatomaceous earth), then isolated by gel filtration (coarse gel (GH25, Amicon) eluted with 0.6 M triethyl-ammonium bicarbonate in 20% isopropanol/water. Half of this material was evaporated to dryness, then evaporated to dryness a further five times from methanol, then deprotected with hydrochloric acid (83 μL, 2N in water)/methanol (2.5 mL) (30 minutes/stirring), and after addition of 0.6 M triethyl-ammonium bicarbonate in 20%. isopropanol/water (2.0 mL) and evaporation to dryness, the deprotected cluster was isolated by gel filtration in the same manner as previously.

Preparation of Di Palmitoyl Phosphatidyl Ethanolamine (DPPE)—Platinum Cluster Conjugate An estimated 30 nmol of the amino-functionalized large platinum cluster dissolved in 0.6 M triethyl-ammonium bicarbonate in 20% isopropanol/water was evaporated to dryness five times from methanol, then dissolved in methanol with a small amount of triethylamine added (pH meter reading between 7.5 and 8.0) (0.6 mL), in which a 200-fold excess of bis(sulfo-succinimidyl) suberate (2.6 mg) was dissolved. This mixture was incubated at room temperature for 1 hour 30 minutes, then the activated cluster was separated over a coarse gel filtration column (Amicon, GH25: length=50 cm, internal diameter=1.0 cm, volume=40 mL), eluted with methanol; the dark brown activated cluster is the first species to elute. Fractions containing uncontaminated activated cluster were combined, solution of DPPE (estimated 100-fold excess: 1 mg) in one-half this volume of trichloromethane was added, and the mixture incubated at 4° C. overnight.

The reaction mixture was evaporated to dryness, redissolved in a 2:1 methanol/chloroform mixture (1.0 mL), then separated by gel filtration on a column identical to that used above for the cluster activation, eluted with the same solvent mixture. The dark brown platinum cluster DPPE conjugate is the first species to be eluted; unconjugated DPPE is eluted later.

The platinum cluster-DPPE conjugate was evaporated to dryness, then shaken in a chloroform-water mixture which contained a small amount of methanol as a phase-transfer agent.

Liposomes containing the lipid-cluster conjugate were prepared by evaporating a chloroform solution of the cluster lipid to dryness, then adding water and sonicating the mixture in a liposome preparation bath. Formation of liposomes was indicated by the generation of a color in the solution upon sonication as liposomes were formed and suspended.

Preparation of Palmitoyl-Platinum Cluster Conjugate

An estimated 30 nmol of the amino-derivatized 2–3 nm platinum cluster dissolved in 0.6 M triethylammonium bicarbonate in 20% isopropanol/water was evaporated to dryness five times from methanol, then dissolved in 3 mL of diclhoromethane, and treated with 200 nmol of palmitic anhydride. The mixture was stirred for one hour at room temperature, then washed three times with 0.1 M sodium phosphate buffer at pH 6.5. The remaining reaction mixture was evaporated to dryness, redissolved in 2:1 methanol/chloroform, then separated by gel filtration (GH25, Amicon eluted with 2:1 methanol:chloroform); the first species to elute is the dark brown palmitamido-platinum cluster. After evaporation to dryness, lipid conjugation was demonstrated by the extraction of the cluster into the chloroform layer when the palmitoyl cluster was shaken in a chloroform/water mixture with a small amount of methanol as a phase transfer agent.

Liposomes containing the lipid-cluster conjugate were prepared by evaporating a chloroform solution of the cluster lipid to dryness, then adding water and sonicating the mixture in a liposome preparation bath. Formation of liposomes was indicated by the generation of a color in the solution upon sonication as liposomes were formed and suspended.

Preparation of Di Palmitoyl Phosphatidyl Ethanolamine (DPPE)—Palladium Cluster Conjugate Preparation and testing followed the same procedure used for the platinum cluster. Estimated 30 nmol of the amino-functionalized large palladium cluster was evaporated to dryness five times from methanol, then dissolved in methanol with a small amount of triethylamine added (pH meter reading between 7.5 and 8.0) (0.6 mL), with a 200-fold excess of bis (sulfo-succinimidyl_) suberate (2.6 mg). This mixture was incubated at room temperature for 1 hour 30 minutes, then the activated cluster was separated by gel filtration (Amicon, GH25: length=50 cm, internal diameter= 1.0 cm, volume=40 mL, eluted with methanol), fractions containing uncontaminated activated cluster were combined, a solution of DPPE (estimated 100-fold excess: 1 mg) in one-half this volume of trichloromethane was added, and the mixture incubated at 4° C. overnight.

The reaction mixture was evaporated to dryness, redissolved in a 2:1 methanol/chloroform mixture (1.0 mL), then separated by gel filtration on a column identical to that used above for the cluster activation, eluted with the same solvent mixture. The dark brown palladium cluster-DPPE conjugate is the first species to be eluted. The cluster-DPPE conjugate was evaporated to dryness, then shaken in a chloroform-water mixture; substitution with the lipid was demonstrated by the extraction of the cluster into the chloroform layer when the DPPE-palladium cluster conjugate was shaken in a chloroform/water mixture with a small amount of methanol as a phase transfer agent.

Liposomes containing the lipid-cluster conjugate were prepared by evaporating a chloroform solution of the cluster lipid to dryness, then adding water and sonicating the mixture in a liposome preparation bath. Formation of liposomes was indicated by the generation of a color in the solution upon sonication as liposomes were formed and suspended.

Preparation of Palmitoyl-Platinum Cluster Conjugate

Preparation used the same procedure as the platinum cluster conjugate: an estimated 30 nmol of amino-derivatized 2–3 nm palladium cluster, dissolved in 0.6 M triethylammonium bicarbonate in 20% isopropanol/water, was evaporated to dryness five times from methanol, dissolved in 3 mL of dichloromethane, then treated with 200 nmol of palmitic anhydride. The mixture was stirred for one hour at room temperature, washed three times with 0.1 M sodium phosphate buffer at pH 6.5, evaporated to dryness, redissolved in 2:1 methanol/chloroform and separated by gel filtration (GH25, Amicon, eluted with 2:1 methanol:chloroform). After evaporation to dryness, lipid conjugation was demonstrated by extraction of the cluster label into the chloroform layer when the palmitoyl palladium cluster conjugate was shaken in a chloroform/water mixture with a small amount of methanol as a phase transfer agent.

Liposomes containing the lipid-cluster conjugate were prepared by evaporating a chloroform solution of the metal cluster lipid to dryness, then adding water and sonicating the mixture in a liposome preparation bath. Formation of liposomes was indicated by the generation of a color in the solution upon sonication as liposomes were formed and suspended.

Preparation of Larger Gold Cluster

A highly monodisperse gold cluster of a size slightly larger than Nanogold, green in color, was prepared by the reduction of a mixture of the gold (I) chloride adducts with ligands 5 and 6 at an elevated temperature of 40° C. This results in a mixture of different sized gold clusters, from which the uniform green species was separated by gel filtration (Pharmacia Superose-12 gel eluted, with aqueous 0.02 M sodium phosphate buffer with 150 mm sodium chloride). The desired green species was eluted with a lower retention time with Nanogold, and is therefore larger. The monoamino-species was separated using ion exchange chromatography.

The monoamino-derivative was converted to the palmitoyl derivative by reaction with excess palmitic anhydride in the same manner as for the large platinum clusters an estimated 30 nmol of monoamino-cluster, dissolved in 0.6 M triethylammonium bicarbonate in 20% isopropanol/water, was evaporated to dryness five times from methanol, dissolved in 3 mL of dichloromethane, then treated with 200 mmol of palmitic anhydride. The mixture was stirred for one hour a room temperature, washed three times with 0.1 M sodium phosphate buffer at pH 6.5, evaporated to dryness, redissolved in 2:1 methanol/chloroform and separated by gel filtration (GH25, Amicon, eluted with 2:1 methanol:chloroform). After evaporation to dryness, lipid conjugation was demonstrated by the extraction of the cluster-labeled lipid into the organic phase when the conjugate was shaken in a chloroform/water mixture with a small amount of methanol as a phase transfer agent.

Liposomes containing the lipid-cluster conjugate were prepared by evaporating a chloroform solution of the metal cluster lipid to dryness, then adding water and sonicating the mixture in a liposome preparation bath. Formation of liposomes was indicated by the generation of a color in the solution upon sonication as liposomes were formed and suspended.

What is claimed is:

1. A metal organothiol particle having the formula $M_n(SR)_m$
   wherein M represents a cluster of metal atoms selected from the group consisting of Au, Ag, Pt, Pd, Tl, and combinations thereof, said cluster forming a central core of said particle,
   wherein n is an integer at least equal to 50,
   wherein $(SR)_m$ represents one or more organothiol moieties which may be the same or different, and
   wherein said organothiol moieties form an outer shell covalently linked to said central core through the sulfur atom of each of said organothiol moieties.

2. The particle of claim 1 wherein each of said organothiol moieties is selected from the group consisting of alkyl thiol, aryl thiol, glutathione, thioglucose, mercaptobenzoic acid, nonylmercaptan, thiol benzoic acid, proteins containing thiol, peptides containing thiol, antibodies and antibody fragments containing thiol, and nucleic acids containing thiol.

3. The particle of claim 1, wherein M is Au and the organothiol moiety is thioglucose.

4. The particle of claim 1, wherein M is Au and the organothiol moiety is glutathione.

5. The particle of claim 1, wherein M is Au and the organothiol moiety is a mixture of glutathione and thioglucose.

6. The particle of claim 1, wherein M is Ag and the organothiol moiety is thioglucose.

7. The particle of claim 1, wherein M is a mixture of Au and Ag and the organothiol moiety is thioglucose.

8. The particle of claim 1, wherein M is Pt and the organothiol moiety is thioglucose.

9. The particle of claim 1, wherein M is Tl and the organothiol moiety is thioglucose.

10. The particle of claim 1, wherein M is Au and the organothiol moiety is o-mercaptobenzoic acid.

11. The particle of claim 1, wherein M is Au and the organothiol moiety is a mixture of o-mercaptobenzoic acid and nonylmercaptan.

12. The particle of claim 1, wherein the central core has a diameter of about 1–3 nm.

13. A functionalized conjugate comprising the metal organothiol particle of claim 1 covalently linked through said organothiol moiety to one or more other molecules selected from the group consisting of antibodies, antibody fragments, lipids, carbohydrates, nucleic acids, peptides, and proteins.

14. The functionalized conjugate of claim 13 wherein the organothiol moiety is covalently linked to IgG.

15. The functionalized conjugate of claim 13 wherein the organothiol moiety is covalently linked to Fab' antibody fragment.

16. The functionalized conjugate of claim 13 wherein the organothiol moiety is covalently linked to an oligonucleotide.

17. A process for making the metal organothiol particle of claim 1 comprising, in a suitable solvent, mixing a metal salt or a metal acid containing M, as defined in claim 1, with an organic thiol compound containing SR, as defined in claim 1, and thereafter adding a reducing agent to said mixture to produce said metal organothiol particle.

18. The process of claim 17 wherein said reducing agent is $NaBH_4$.

19. The process of claim 17 wherein said metal salt or metal acid is selected from $HAuCl_4$, $KAuBr_4$, $PtCl_4$, thallium chloride and silver acetate.

20. The process of claim 17 further comprising incubating said metal organothiol particle with a second organic thiol compound thereby replacing one or more of said organothiol moieties already covalently linked to said central core with an organothiol moiety from said second organic thiol compound.

21. The process of claim 20 wherein said second organic thiol compound is selected from the group consisting of IgG, Fab' antibody fragments, proteins containing thiol, peptides containing thiol, carbohydrates containing thiol, lipids containing thiols, nucleic acids containing thols, alkyl thiol compounds and aryl thiol compounds.

22. A process for making the metal organothiol particle of claim 1 comprising dissolving a preformed metal-organothiol compound containing M and SR, as defined in claim 1, in a suitable solvent, and adding a reducing agent to produce said metal organothiol particle.

23. The process of claim 22 wherein said reducing agent is $NaBH_4$.

24. The process of claim 22 further comprising incubating said metal organothiol particle with a a second organic thiol compound thereby replacing one or more of said organothiol moieties already covalently linked to said central core with an organothiol moiety from said second organic thiol compound.

25. The process of claim 24 wherein said second organic thiol compound is selected from the group consisting of IgG, Fab' antibody fragments, proteins containing thiol, peptides containing thiol, carbohydrates containing thiol lipids containing thiols, nucleic acids containing thiols, alkyl thiol compounds, and aryl thiol compounds.

* * * * *